United States Patent [19]
Mothersole et al.

[11] Patent Number: 4,633,437
[45] Date of Patent: Dec. 30, 1986

[54] DATA PROCESSOR HAVING DYNAMIC BUS SIZING

[75] Inventors: David S. Mothersole, Austin, Tex.; Lester M. Crudele, Groton, Mass.; James L. Tietjen; Robert R. Thompson, both of Austin, Tex.

[73] Assignee: Motorola, Inc., Schaumburg, Ill.

[21] Appl. No.: 624,660

[22] Filed: Jun. 26, 1984

[51] Int. Cl.⁴ .............................................. G06F 9/00
[52] U.S. Cl. ................................................... 364/900
[58] Field of Search ... 364/200 MS File, 900 MS File

[56] References Cited
U.S. PATENT DOCUMENTS
4,309,754  1/1982  Dinwiddie, Jr. ..................... 364/200

Primary Examiner—Thomas M. Heckler
Assistant Examiner—John G. Mills
Attorney, Agent, or Firm—John A. Fisher; Jeffrey Van Myers

[57] ABSTRACT

In a data processor adapted to perform operations upon operands of a given size, a bus controller is provided to communicate the operands with a storage device having a data port which may be a submultiple of the operand size. In response to a signal from the bus controller requesting the transfer of an operand of a particular size, the storage device provides a size signal indicating the size of the data port available to accommodate the requested transfer. Depending upon the size of the operand to be transferred and the size of the data port of the storage device, the bus controller may break the operand transfer cycle into several bus cycles in order to completely transfer the operand. In the process, the bus controller compensates for any address misalignment between the operand and the data port. In order to distinguish individual operand cycles from the several bus cycles which may comprise the operand cycle, the bus controller provides an operand cycle start signal only at the start of the first bus cycle of each operand cycle.

18 Claims, 32 Drawing Figures

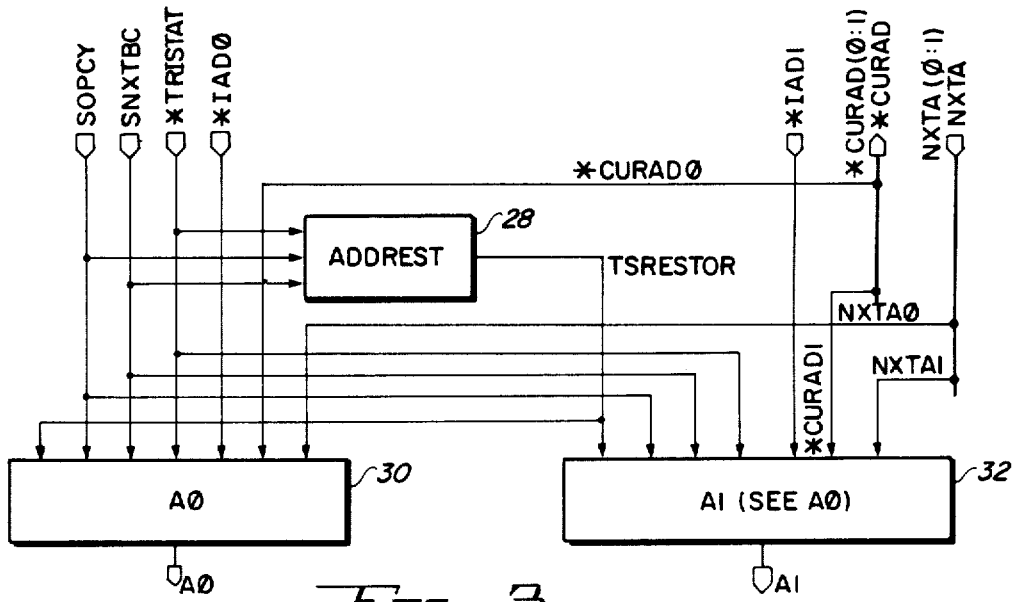
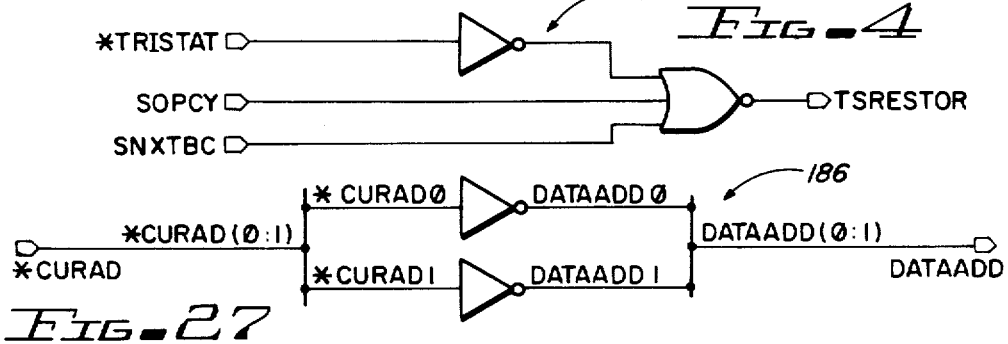
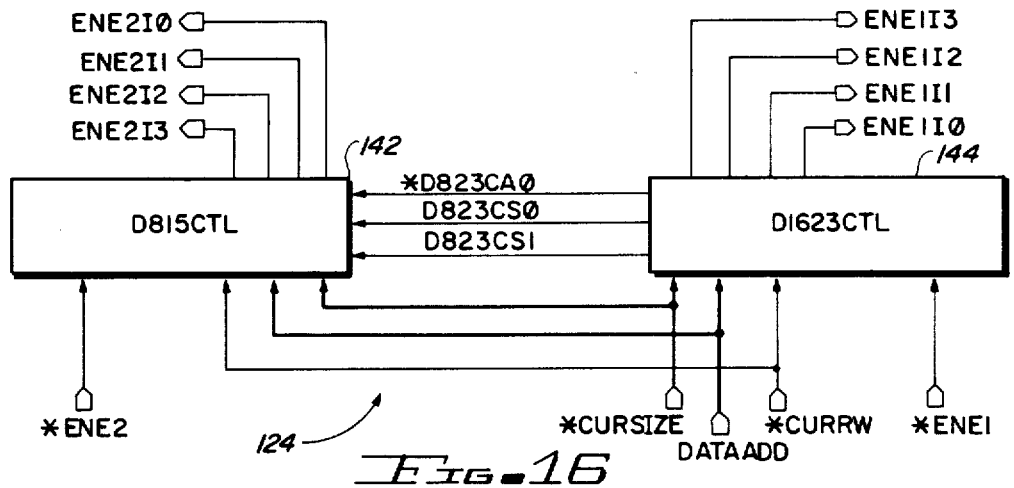

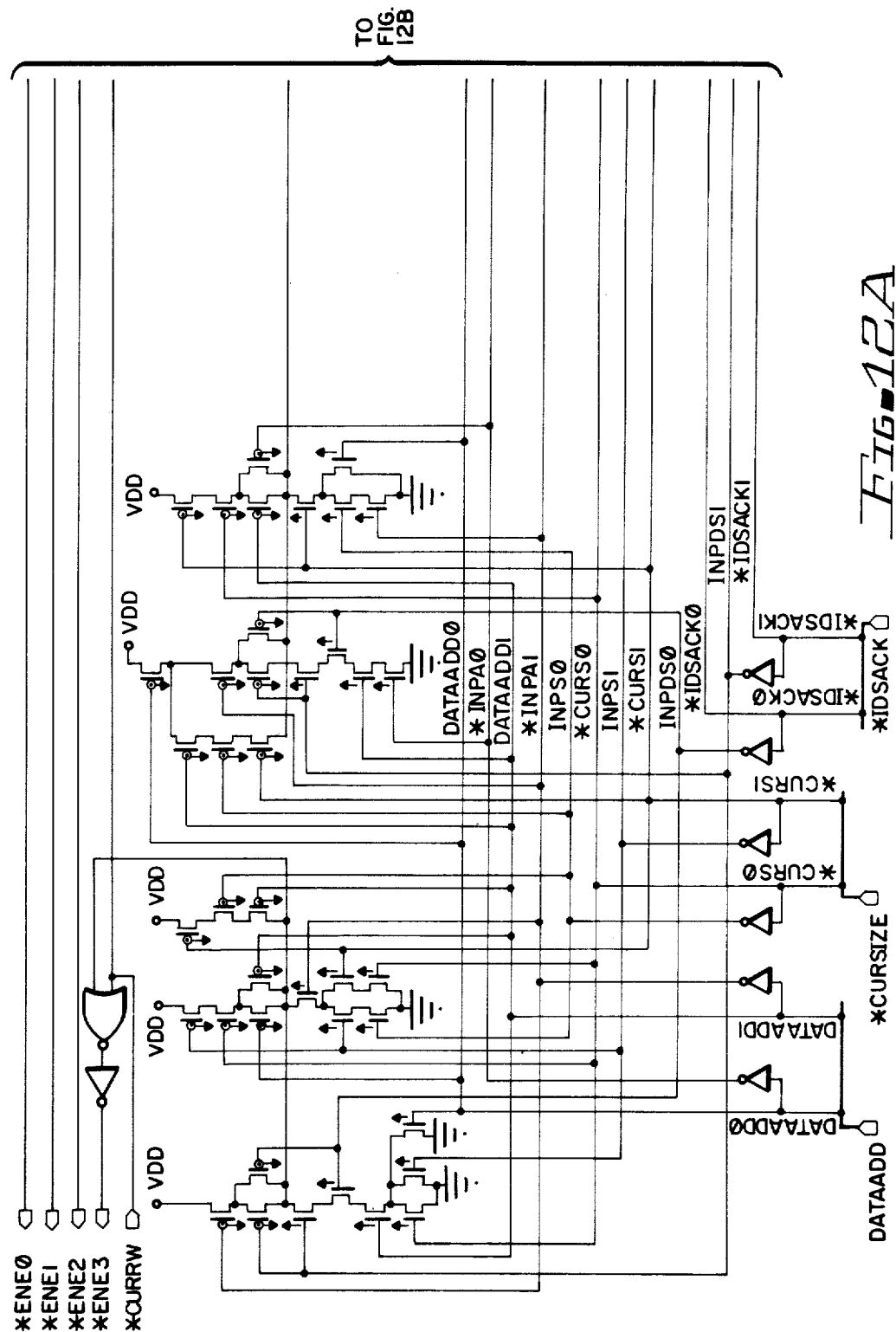

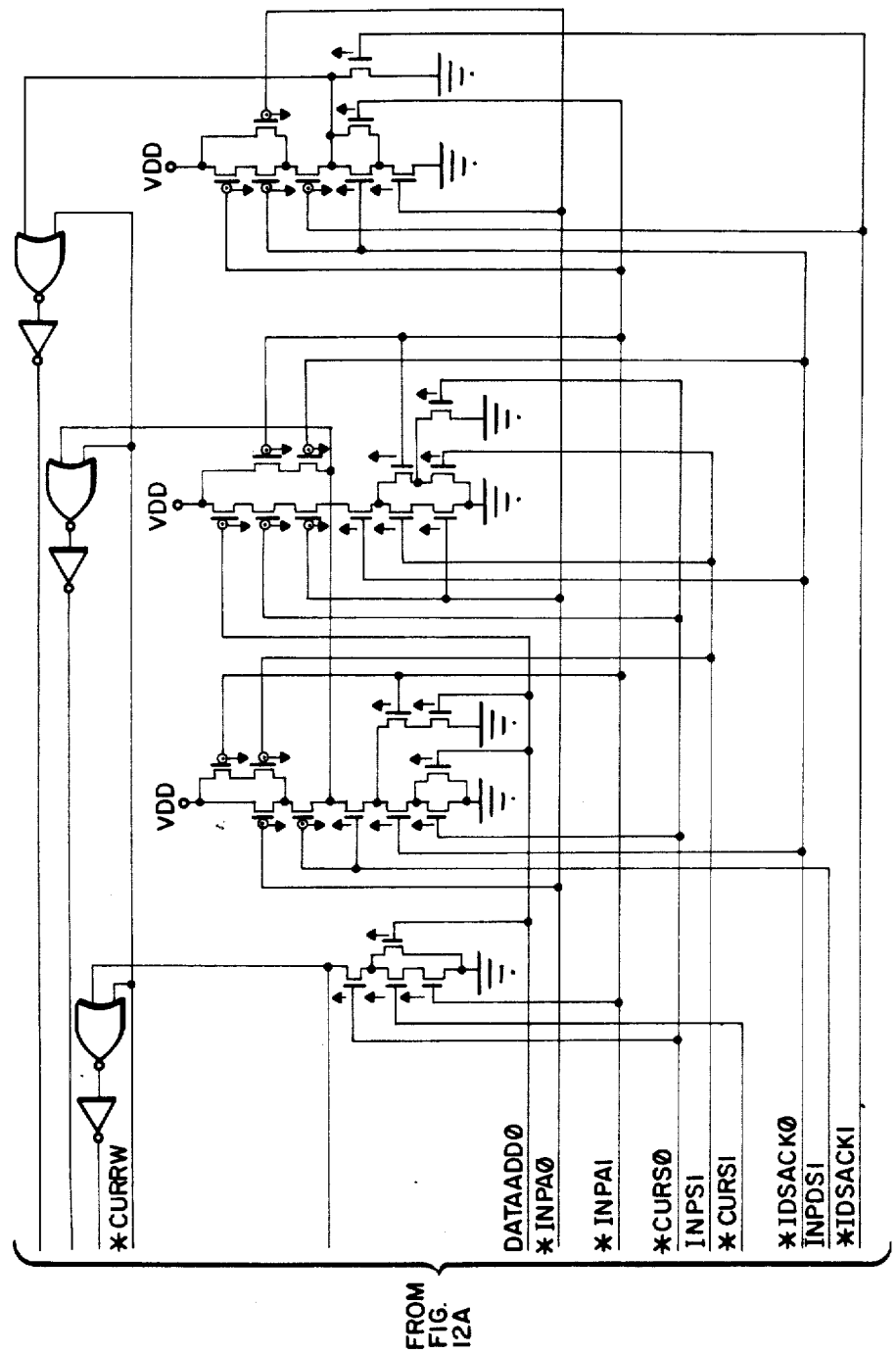

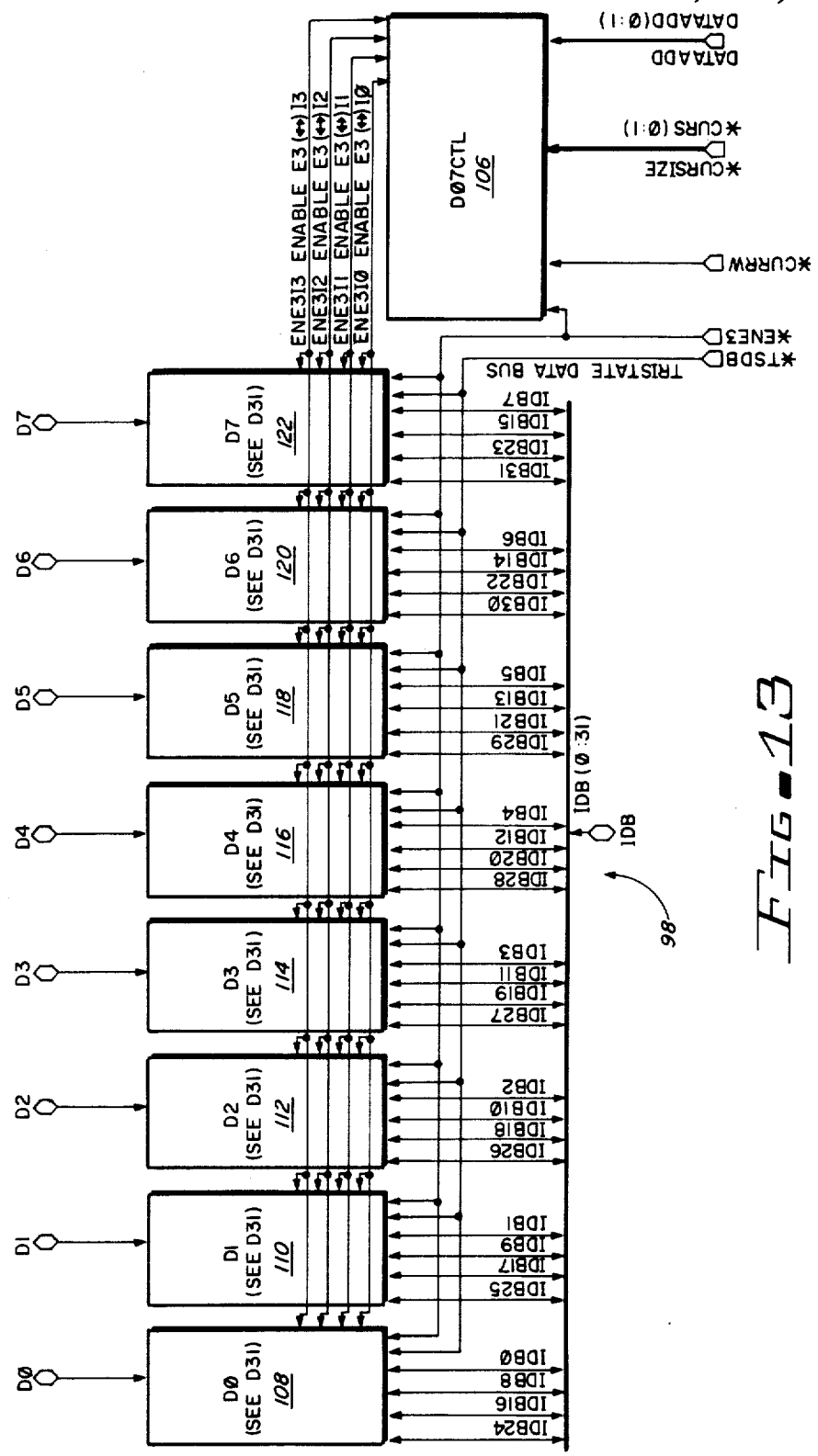

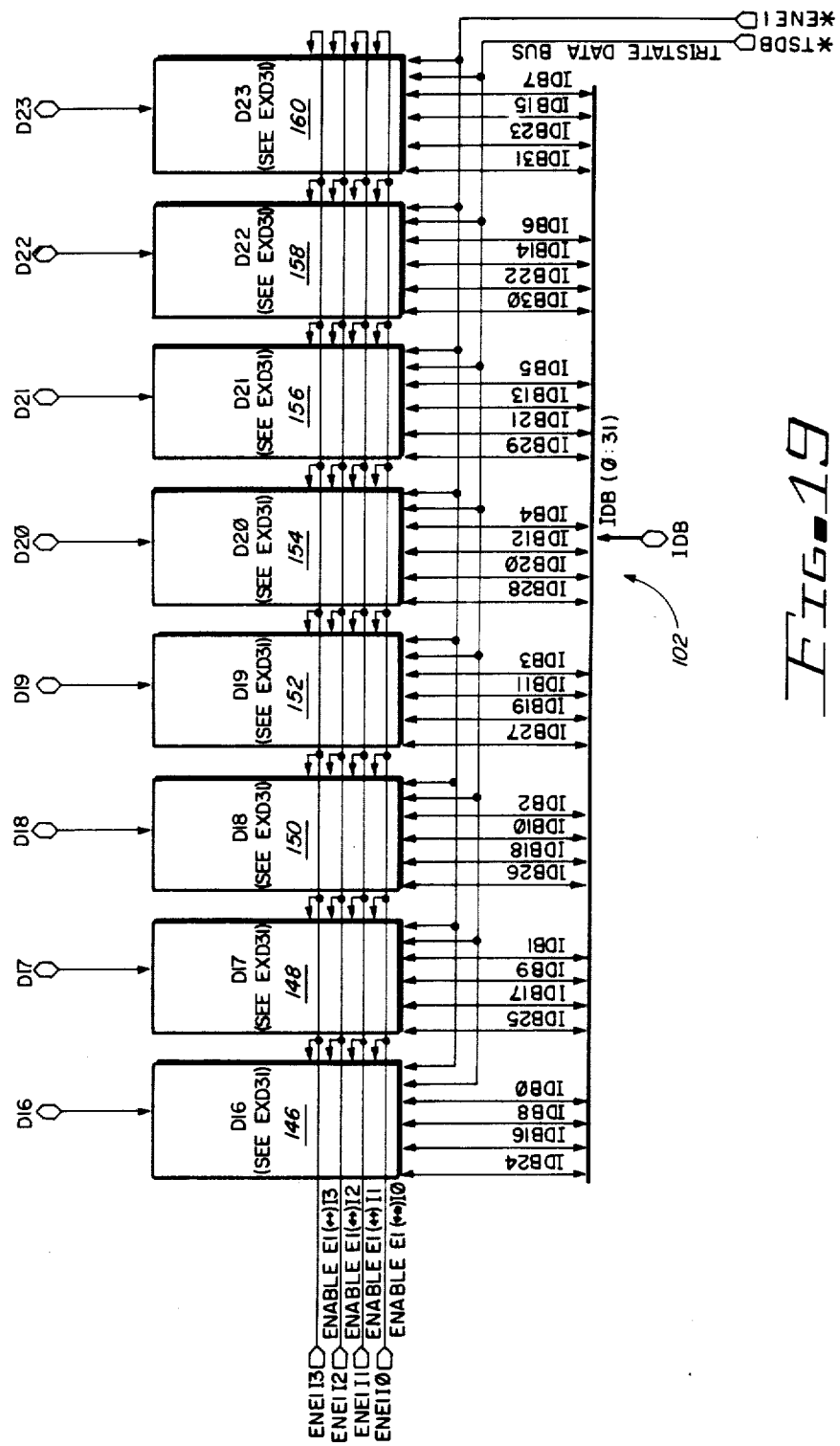

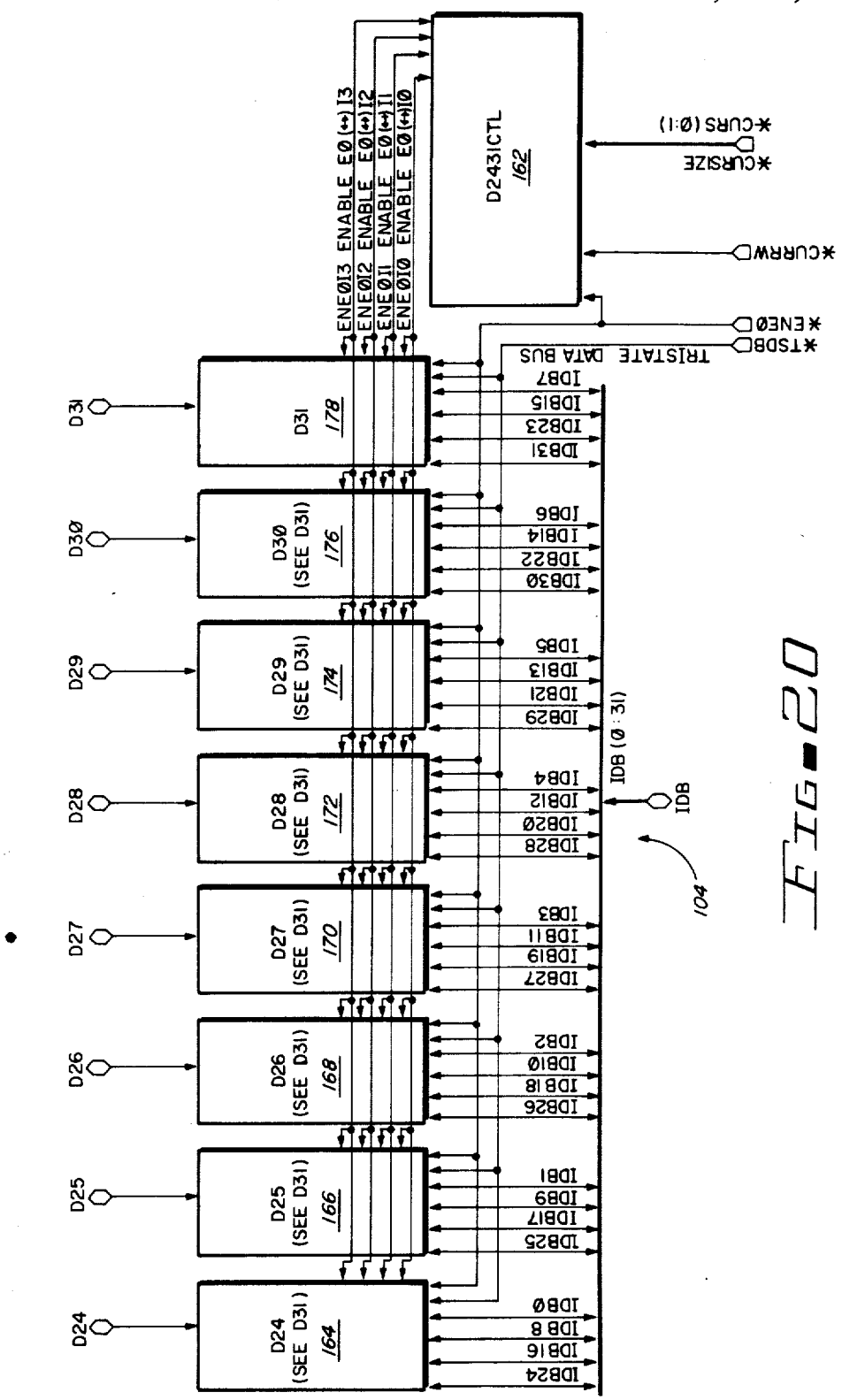

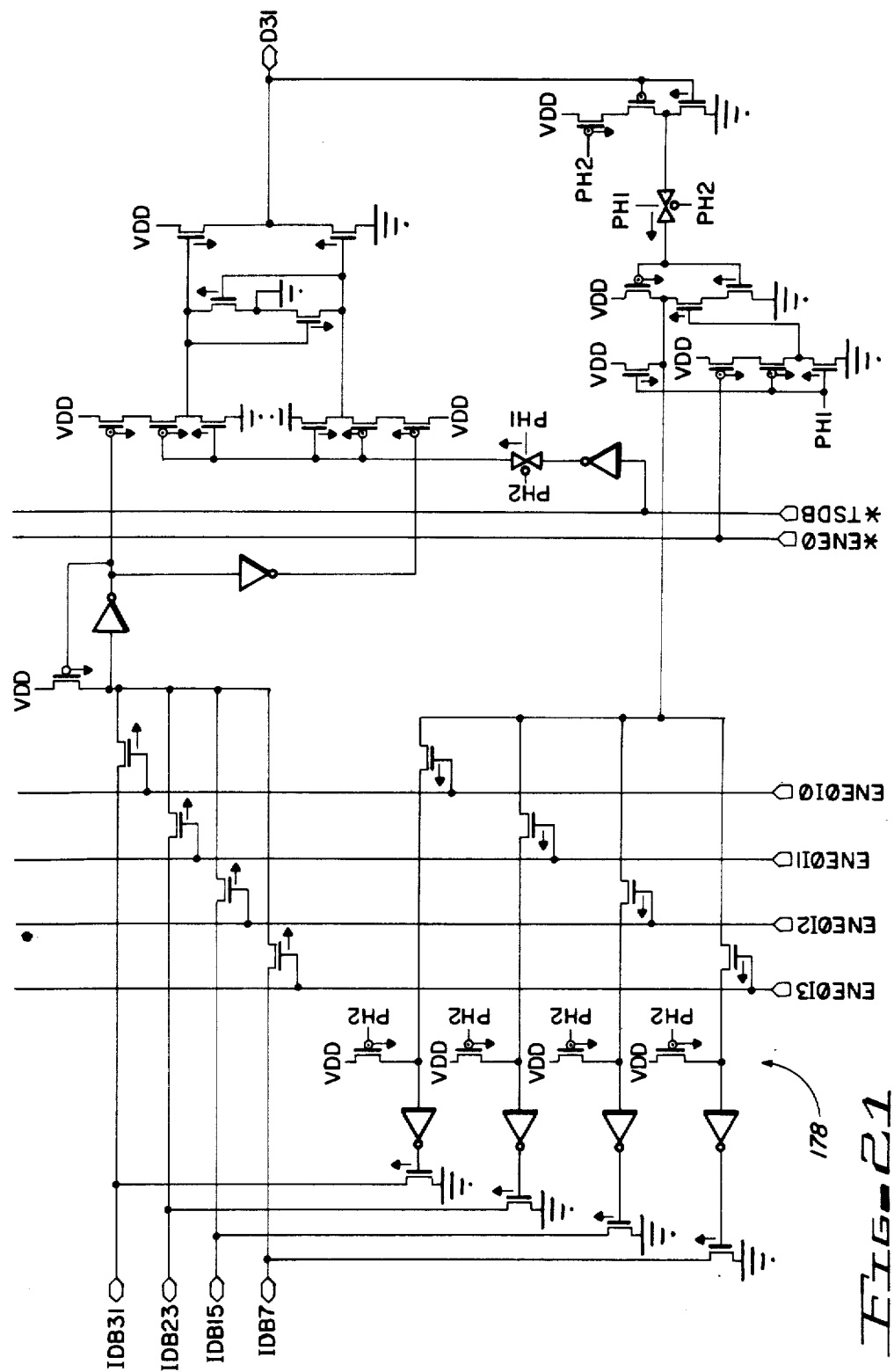

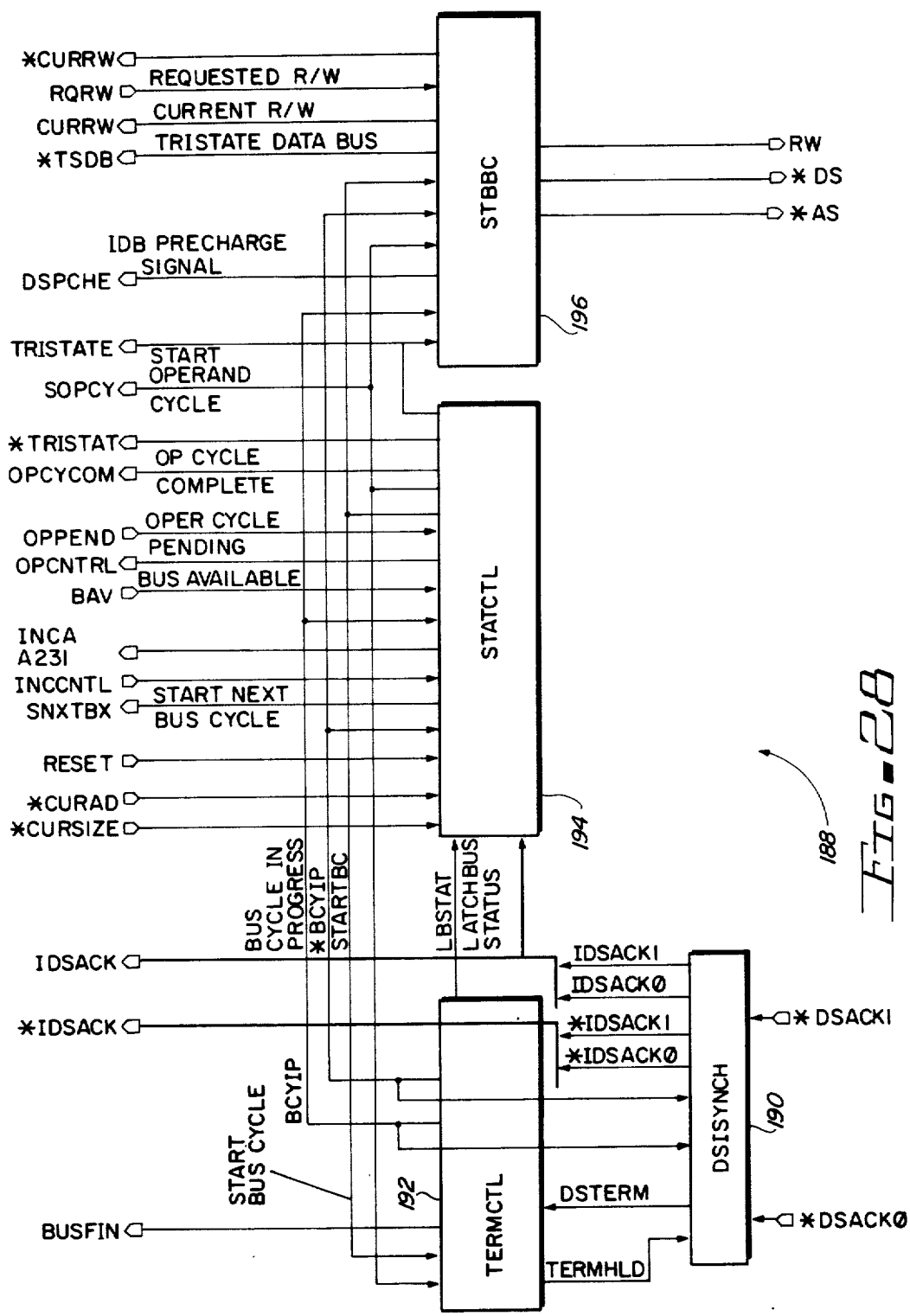

DATA PROCESSOR HAVING DYNAMIC BUS SIZING

CROSS REFERENCE TO RELATED APPLICATIONS

Related subject matter is disclosed in U.S. patent application Ser. No. 625,068, now continued as U.S. patent application Ser. No. 861,742, both entitled DATA PROCESSOR HAVING MULTIPLE BUS CYCLE OPERAND CYCLES, inventors David S. Mothersole, Jay Alen Hartvigsen and Robert R. Thompson, filed on xx June 1984, and assigned to the Assignee hereof

FIELD OF THE INVENTION

The present invention relates generally to data processors and, more particularly, to a data processor which is capable of communicating with system resources having different data port sizes.

BACKGROUND OF THE INVENTION

In general, data processors communicate with all of the different types of system resources using the same communication bus. For example, the data processor would communicate with both the primary and the secondary memories using the same communication bus. Similarly, the same communication bus would be used to communicate with input/output controllers and the like. If communication is necessary in a particular system with a resource which is unable to utilize the existing common communication bus because of data port size incompatibility, an interface adapter must be employed to buffer data transfers between the processor's bus and that of the resource. In addition to adding additional circuitry to the system, the interface devices require that the data processor provide specific directions for each such transfer.

SUMMARY OF THE INVENTION

Accordingly, it is an object of the present invention to provide a data processor having a bus controller which is able to communicate with any of a plurality of system resources having different data port sizes, using a communication bus which is a common multiple of these port sizes.

More generally, it is an object of the present invention to provide the capability in any bus master to communicate with any of a plurality of available bus slaves having different data port sizes, using a communication bus which is a common multiple of these port sizes.

These and other objects are accomplished in a data processor adapted to communicate with a storage device having any of a plurality of different data port sizes using a communication bus which is sized to accomodate each of the different port sizes. In the preferred form, the data processor comprises: a first logic circuit which provides to the storage device a strobe signal indicating that an operand is to be communicated using the communication bus; a second logic circuit which receives an acknowledge signal, provided by the storage device in response to the strobe signal, indicating that the storage device is prepared to communicate the operand with the data processor using a portion of the communication bus corresponding to a selected one of the different port sizes; and a third logic circuit which communicates the operand between the data processor and the storage device in as many units of the selected port size as are required to completely communicate the operand, using the portion of the communication bus which corresponds to the selected port size.

In a more general sense, the present invention may be used to adapt any bus master to communicate with a bus slave having any of a plurality of different port sizes using a communication bus which is sized to accomodate each of the different port sizes. In this generic form, the bus master would comprise: a first logic circuit which provides to the bus slave a strobe signal indicating that an operand is to be communicated using the communication bus; a second logic circuit which receives an acknowledge signal, provided by the bus slave in response to the strobe signal, indicating that the bus slave is prepared to communicate the operand with the bus master using a portion of the communication bus corresponding to a selected one of the different port sizes; and a third logic circuit which communicates the operand between the bus master and the bus slave, in as many units of the selected port size as are required to completely communicate the operand, using the portion of the communication bus which corresponds to the selected port size.

BRIEF DESCRIPTION OF THE DRAWINGS

FIG. 3 is a block diagram of the A0 and A1 interfaces of the address bus interface of FIG. 2.

FIG. 4 is a detailed schematic of the address restore portion of the A0/A1 interface of FIG. 3.

FIG. 12 is a detailed schematic diagram of the input enable portion of the data bus interface of FIG. 10.

FIG. 13 is a block diagram of the D0 through D7 interfaces of the data bus interface of FIG. 10.

FIG. 18 is a detailed schematic diagram of the control for the D16-D23 interfaces of the data bus interface of FIG. 16.

FIG. 19 is block diagram of the D16 through D23 interfaces of the data bus interface of FIG. 10.

FIG. 20 is a block diagram of the D24 through D31 interfaces of the data bus interface of FIG. 10.

FIG. 21 is a detailed schematic diagram of the D31 interface of the data bus interface of FIG. 20, all of the other interfaces D0 through D30 being identical.

FIG. 27 is a detailed schematic diagram of the data address buffers of the bus controller of FIG. 23.

FIG. 28 is a block diagram of the microsequencer of the bus controller of FIG. 23.

DESCRIPTION OF THE INVENTION

Figure 1:
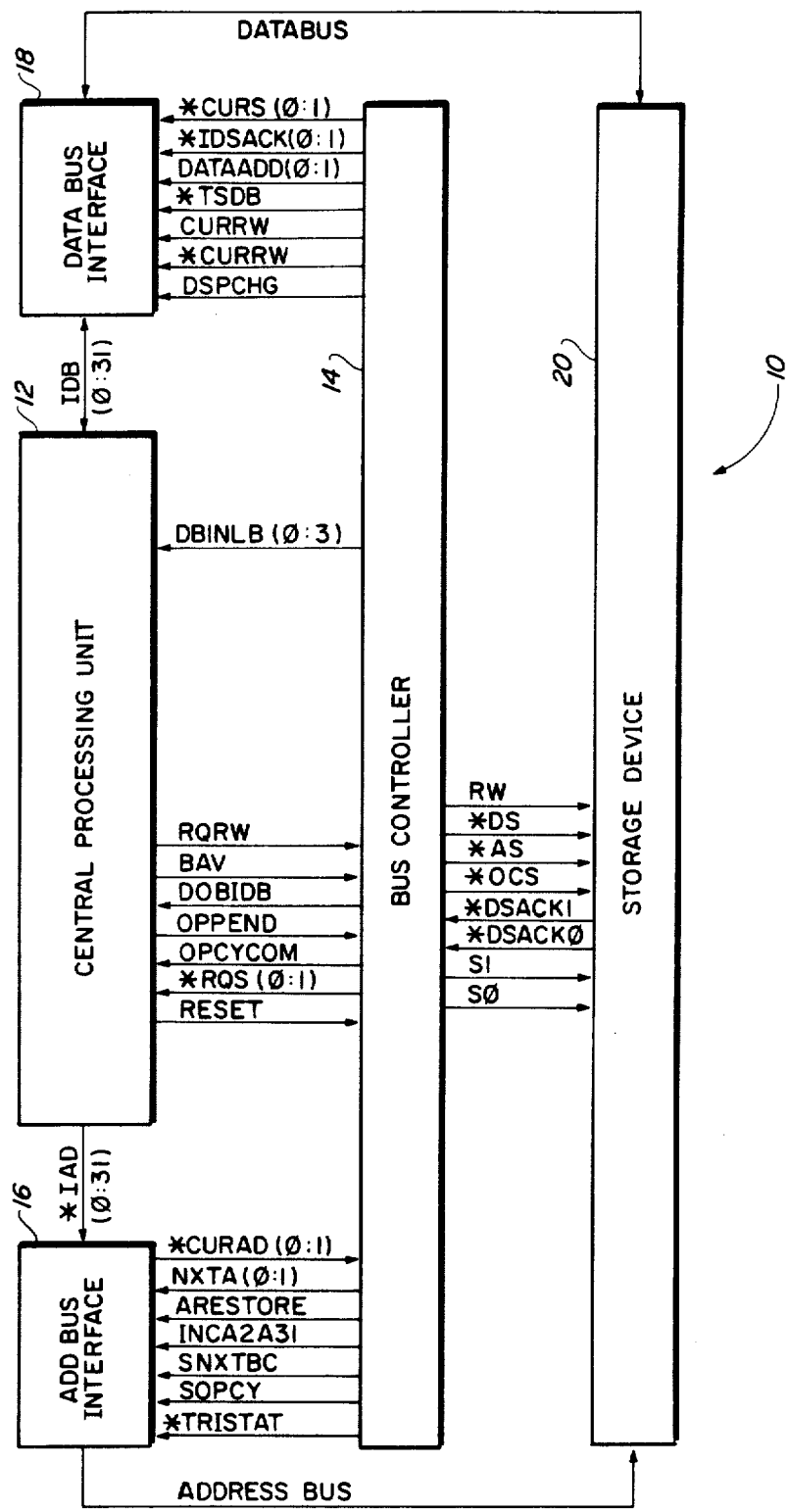
FIG. 1 is a block diagram of a data processor having a bus controller constructed in accordance with the present invention.

Shown in FIG. 1 is a data processor 10 comprising a central processing unit (CPU) 12, a bus controller 14, an address bus interface 16, a data bus interface 18, and a storage device 20. In general, the CPU 12 executes a user specified sequence of instructions, each of which is comprised of one or more 16-bit words. Each of these instructions must be read from the storage device 20 in the appropriate sequence. In the course of executing each such instruction, the CPU 12 may be required to perform a specified operation upon an 8-bit byte, a 16-bit word or a 32-bit long word. Most of these data operands must be either read from or written to the storage device 20. In order to assure optimum performance on long word operations, the CPU 12 is provided with a 32-bit data port. On the other hand, it may be advantageous (or unavoidable) that the storage device 20 have a data port which is smaller than that of the CPU 12. Even when the port sizes are the same, the operand required by the CPU 12 may still reside at an address within the storage device 20 which does not align evenly with the data port of that particular storage device 20. It is the responsibility of the bus controller 14 to coordinate the activities of the address bus interface 16 and the data bus interface 18 in actually transfering the requested data or instruction operands between the CPU 12 and the storage device 20, regardless of operand misalignment or any mismatch between the port sizes of the CPU 12 and the storage device 20.

In general, the CPU 12 requests an operand transfer by asserting an OPeration-PENDing signal (OPPEND) to the bus controller 14. Simultaneously, the CPU 12 will provide a Read/Write-ReQuest signal (RQRW) indicating the direction of operand transfer and a Requested-Size signal (*RQS[0:1]) indicating the size of the operand to the transferred. The CPU 12 also provides a 32-bit Address (A[0:31]) to or from which the operand is to be transferred on a 32-bit Internal Address Bus (*IAB[0:31]).

Assuming for the moment that the CPU 12 has requested an operand write, the bus controller 14 will briefly assert a Start-OPerand-CYcle signal (SOPCY) directing the address bus interface 16 to latch the operand address on the *IAB. Simultaneously, the bus controller 14 will negate a TRISTATE signal (*TRISTATE) to enable the address bus interface 16 to transfer the address to the storage device 20 on a 32-bit external ADDRESS BUS (ADDRESSBUS). A brief time later, the bus controller 14 will assert an Address-Strobe signal (*AS) to the storage device 20 indicating that a valid operand address is on the ADDRESSBUS.

The bus controller 14 will then assert a Data-Output-Buffer-to-Internal-Data-Bus signal (DOBIDB) directing the CPU 12 to provide the operand to the data bus interface 18 on a 32-bit Internal Data Bus (IDB[0:31]). The bus controller 14 will also provide to the data bus interface 18: a CURrent-Size signal (*CURS[0:1]) indicating the size of the operand to be placed on the DATABUS; a DATA-ADDress signal (DATAADD[0:1]) corresponding to the two low order address bits A0 and A1 of the address on the ADDRESSBUS; and a CURrent-Read/Write signal (*CURRW;CURRW) corresponding to the current state of the RW signal.

In the illustrated form, the IDB is partitioned into four bytes: I0 consisting of internal Data bits D31 through D24; I1 consisting of Data bits D23 through D16; I2 consisting of internal Data bits D15 through D8; and I3 consisting of internal Data bits D7 through D0. Depending upon the size of the operand being transferred, these internal bytes must be selectively coupled to the external DATABUS which is also partitioned into four bytes: E0 consisting of external Data bits D31 through D24; E1 consisting of external Data bits D23 through D16; E2 consisting of external Data bits D15 through D8; and E3 consisting of external Data bits D7 through D0.

Depending upon the current operand size (*CURS[0:1]) and the current operand address (DATAADD[0:1]), the data bus interface 18 will provide the available bytes on the IAB to the appropriate bytes on the DATABUS as follows:

| CURS | | DATAADD | | DATABUS | | | |
|---|---|---|---|---|---|---|---|
| 0 | 1 | 0 | 1 | E0 | E1 | E2 | E3 |
| 0 | 0 | 0 | 0 | I0 | I1 | I2 | I3 |
| 0 | 0 | 0 | 1 | I0 | I0 | I1 | I2 |
| 0 | 0 | 1 | 0 | I0 | I1 | I0 | I1 |
| 0 | 0 | 1 | 1 | I0 | I0 | I1 | I0 |
| 0 | 1 | x | x | I3 | I3 | I3 | I3 |
| 1 | 0 | x | 0 | I2 | I3 | I2 | I3 |
| 1 | 0 | x | 1 | I2 | I2 | I3 | I2 |
| 1 | 1 | 0 | 0 | I1 | I2 | I3 | I0 |
| 1 | 1 | 0 | 1 | I1 | I1 | I2 | I3 |
| 1 | 1 | 1 | 0 | I1 | I2 | I1 | I2 |

-continued

| CURS | | DATAADD | | DATABUS | | | |
|---|---|---|---|---|---|---|---|
| 0 | 1 | 0 | 1 | E0 | E1 | E2 | E3 |
| 1 | 1 | 1 | 1 | \|i1\| | \|i1\| | \|i2\| | \|i1\| | where small "i" indicates a connection for convenience rather than a required connection. After the data bus interface 18 has had sufficient time to establish the operand on the DATABUS, the bus controller 14 will assert a Data-Strobe signal (*DS) to advise the storage device 20 that the operand on the DATABUS is valid.

Upon receiving the Address-Strobe (*AS), the storage device 20 will decode the address on the ADDRESSBUS. If the address is determined to be within the address range for that particular storage device 20, the storage device 20 will prepare to latch the operand. To best facilitate this, the storage device 20 has its data port connected to the DATABUS so that the high order byte (00) of the data port of the storage device 20 will be aligned with the high order byte (E0) of the DATABUS as follows:

| DATAPORT | E0 | E1 | E2 | E3 |
|---|---|---|---|---|
| 32-bits | \|00\| | 01\| | 02\| | 03\| |
| 16-bits | \|00\| | 01\| | | |
| 8-bits | \|00\| | | | |

Thus, upon receiving the DATA-Strobe (*DS), the storage device 20 will always be able to latch at least the high order portion of the operand during the first bus cycle of every operand cycle. After successfully capturing the respective portion of the operand, the storage device 20 will provide a Data-transfer-and-Size-ACKnowledge signal (*DSACK[0:1]) acknowledging the operand transfer. In addition, however, the *DSACK signal also indicates the size of the data port of that particular storage device 20 as follows:

| DSACK | | WIDTH OF DATA PORT |
|---|---|---|
| 0 | 1 | |
| 0 | 0 | (bus cycle incomplete) |
| 0 | 1 | 8-bits |
| 1 | 0 | 16-bits |
| 1 | 1 | 32-bits |

Using the known operand Size (S[0:1]) and CURrent-ADdress (*CURAD[0:1]), and the size of the port (*DSACK[0:1]), the bus controller 14 can determine the size of residual portion of the operand, if any, which has not yet been received, as follows:

| current | | | | returned | | next | | cycle |
|---|---|---|---|---|---|---|---|---|
| S1 | S0 | A1 | A0 | DSACK1 | DSACK0 | S1 | S0 | done? |
| 0 | 1 | 0 | 0 | 0 | 0 | x | x | i |
| 0 | 1 | 0 | 0 | 0 | 1 | x | x | y |
| 0 | 1 | 0 | 0 | 1 | 0 | x | x | y |
| 0 | 1 | 0 | 0 | 1 | 1 | x | x | y |
| 0 | 1 | 0 | 1 | 0 | 0 | x | x | i |
| 0 | 1 | 0 | 1 | 0 | 1 | x | x | y |
| 0 | 1 | 0 | 1 | 1 | 0 | x | x | y |
| 0 | 1 | 0 | 1 | 1 | 1 | x | x | y |
| 0 | 1 | 1 | 0 | 0 | 0 | x | x | i |
| 0 | 1 | 1 | 0 | 0 | 1 | x | x | y |
| 0 | 1 | 1 | 0 | 1 | 0 | x | x | y |
| 0 | 1 | 1 | 0 | 1 | 1 | x | x | y |
| 0 | 1 | 1 | 1 | 0 | 0 | x | x | i |
| 0 | 1 | 1 | 1 | 0 | 1 | x | x | y |
| 0 | 1 | 1 | 1 | 1 | 0 | x | x | y |
| 0 | 1 | 1 | 1 | 1 | 1 | x | x | y |
| 1 | 0 | 0 | 0 | 0 | 0 | x | x | i |
| 1 | 0 | 0 | 0 | 0 | 1 | 0 | 1 | n |
| 1 | 0 | 0 | 0 | 1 | 0 | x | x | y |
| 1 | 0 | 0 | 0 | 1 | 1 | x | x | y |
| 1 | 0 | 0 | 1 | 0 | 0 | x | x | i |
| 1 | 0 | 0 | 1 | 0 | 1 | 0 | 1 | n |
| 1 | 0 | 0 | 1 | 1 | 0 | 0 | 1 | n |
| 1 | 0 | 0 | 1 | 1 | 1 | x | x | y |
| 1 | 0 | 1 | 0 | 0 | 0 | x | x | i |
| 1 | 0 | 1 | 0 | 0 | 1 | 0 | 1 | n |
| 1 | 0 | 1 | 0 | 1 | 0 | x | x | y |
| 1 | 0 | 1 | 0 | 1 | 1 | x | x | y |
| 1 | 0 | 1 | 1 | 0 | 0 | x | x | i |
| 1 | 0 | 1 | 1 | 0 | 1 | 0 | 1 | n |
| 1 | 0 | 1 | 1 | 1 | 0 | 0 | 1 | n |
| 1 | 0 | 1 | 1 | 1 | 1 | 0 | 1 | n |
| 1 | 1 | 0 | 0 | 0 | 0 | x | x | i |
| 1 | 1 | 0 | 0 | 0 | 1 | 1 | 0 | n |
| 1 | 1 | 0 | 0 | 1 | 0 | 0 | 1 | n |
| 1 | 1 | 0 | 0 | 1 | 1 | x | x | y |
| 1 | 1 | 0 | 1 | 0 | 0 | x | x | i |
| 1 | 1 | 0 | 1 | 0 | 1 | 1 | 0 | n |
| 1 | 1 | 0 | 1 | 1 | 0 | x | x | y |
| 1 | 1 | 0 | 1 | 1 | 1 | x | x | y |
| 1 | 1 | 1 | 0 | 0 | 0 | x | x | i |
| 1 | 1 | 1 | 0 | 0 | 1 | 1 | 0 | n |
| 1 | 1 | 1 | 0 | 1 | 0 | 0 | 1 | n |
| 1 | 1 | 1 | 0 | 1 | 1 | 0 | 1 | n |
| 1 | 1 | 1 | 1 | 0 | 0 | x | x | i |
| 1 | 1 | 1 | 1 | 0 | 1 | 1 | 0 | n |
| 1 | 1 | 1 | 1 | 1 | 0 | 1 | 0 | n |
| 1 | 1 | 1 | 1 | 1 | 1 | 1 | 0 | n |
| 0 | 0 | 0 | 0 | 0 | 0 | x | x | i |
| 0 | 0 | 0 | 0 | 0 | 1 | 1 | 1 | n |
| 0 | 0 | 0 | 0 | 1 | 0 | 1 | 0 | n |
| 0 | 0 | 0 | 0 | 1 | 1 | x | x | y |
| 0 | 0 | 0 | 1 | 0 | 0 | x | x | i |
| 0 | 0 | 0 | 1 | 0 | 1 | 1 | 1 | n |
| 0 | 0 | 0 | 1 | 1 | 0 | 1 | 1 | n |
| 0 | 0 | 0 | 1 | 1 | 1 | 0 | 1 | n |
| 0 | 0 | 1 | 0 | 0 | 0 | x | x | p |
| 0 | 0 | 1 | 0 | 0 | 1 | 1 | 1 | n |
| 0 | 0 | 1 | 0 | 1 | 0 | 1 | 0 | n |
| 0 | 0 | 1 | 0 | 1 | 1 | 1 | 0 | n |
| 0 | 0 | 1 | 1 | 0 | 0 | x | x | i |
| 0 | 0 | 1 | 1 | 0 | 1 | 1 | 1 | n |
| 0 | 0 | 1 | 1 | 1 | 0 | 1 | 1 | n |
| 0 | 0 | 1 | 1 | 1 | 1 | 1 | 1 | n | where:
x = > don't care
i = > bus cycle incomplete
y = > operand cycle complete
n = > operand cycle incomplete Thus, for example, if the port size of the storage device 20 is the same as the size of the DATABUS or if the size of the operand is less than or equal to the port size of the storage device 20, the bus controller 14 will know that all of the operand has been received and that the operand cycle can be terminated. At this time, if another bus master (not shown) is awaiting use of the communication bus, the bus controller 14 will assert the *TRISTATE signal to force the address bus interface 16 to remove the address from the ADDRESSBUS. In any event, the bus controller 14 will then assert a Tristate-Data-Bus signal (*TSDB) to force the data bus interface 18 to remove the operand from the DATABUS. Simultaneously, the bus controller 14 will assert an OPerand-CYcle-COMplete signal (OPCYCOM) to advise the CPU 12 that the requested operand write has been completed. Finally, the bus controller 14 will terminate the bus cycle by negating the Address and Data Strobes (*AS and *DS). In response, the storage device 20 will withdraw the *DSACK signal. At this time, the communication bus again becomes available for use by the CPU 12 or any other bus master (not shown) which may be present in the system.

If additional bus cycles are required to complete the operand cycle, the bus controller 14 will recompute the two low order bits A0 and A1 of the address of the residual operand as follows:

| CURAD | | DSACK | | NXTA | | address rollover? |
|---|---|---|---|---|---|---|
| 1 | 0 | 1 | 0 | 1 | 0 | |
| 0 | 0 | 0 | 0 | x | x | p |
| 0 | 0 | 0 | 1 | 0 | 1 | n |
| 0 | 0 | 1 | 0 | 1 | 0 | n |
| 0 | 0 | 1 | 1 | x | x | x |
| 0 | 1 | 0 | 0 | x | x | p |
| 0 | 1 | 0 | 1 | 1 | 0 | n |
| 0 | 1 | 1 | 0 | 1 | 0 | n |
| 0 | 1 | 1 | 1 | 0 | 0 | y |
| 1 | 0 | 0 | 0 | x | x | p |
| 1 | 0 | 0 | 1 | 1 | 1 | n |
| 1 | 0 | 1 | 0 | 0 | 0 | y |
| 1 | 0 | 1 | 1 | 0 | 0 | y |
| 1 | 1 | 0 | 0 | x | x | p |
| 1 | 1 | 0 | 1 | 0 | 0 | y |
| 1 | 1 | 1 | 0 | 0 | 0 | y |
| 1 | 1 | 1 | 1 | 0 | 0 | y | where:
x = > don't care
p = > bus cycle incomplete
n = > no address rollover
y = > address rollover.

The bus controller 14 will then provide a NeXT-Address signal (NXTA[0:1]) to the address bus interface 16 indicating the new low order address bits A0 and A1. If the communication bus has been used by a different bus master (not shown) since the previous bus cycle of the current operand cycle, the bus controller 14 will assert an Address-Restore signal (ARESTORE) requesting the address bus interface 16 to restore the original higher order address bits (*IAD[2:31]), but use the two new low order address bits (NXTA[0:1]). On the other hand, if the new address bits have rolled over, the bus controller 14 will assert an INCrement-A2-through-A31 signal (INCA2A31) requesting the address bus interface 16 to increment the original higher order address bits (*IAD[2:31]), and use the incremented address together with the two new low order address bits (NXTA[0:1]). In anticipation of this request, the address bus interface 16 has already incremented the higher order address bits A2–A31. Thus, the bus controller 14 can immediately assert a Start-NeXT-Bus-Cycle signal (SNXTBC) requesting the address bus interface 16 to start the next bus cycle using the new address. From this point on, the bus controller 14 cooperates with the address bus interface 16 and the data bus interface 18 as described above. If necessary, this sequence is repeated until all of the requested operand has been received and latched into the storage device 20.

In general, the write operand cycle can be summarized with respect to any bus master writing an operand to a bus slave as follows:

BUS MASTER:
(1) Set Read/Write (RW) to Write
(2) Drive Address on ADDRESSBUS
(3) Drive Size (S[0:1])
(4) Assert Address-Strobe (*AS)
(5) Drive operand byte(s) on DATABUS
(6) Assert Data-Strobe (*DS)

BUS SLAVE:
(1) Decode Address on ADDRESSBUS
(2) Latch operand byte(s) on DATABUS
(3) Assert Data-transfer-and-Size-ACKnowledge (*DSACK[0:1])

BUS MASTER:
(7) Negate Data-Strobe (*DS)
(8) Negate Address-Strobe (*AS)
(9) Remove operand byte(s) from DATABUS BUS SLAVE
(4) Negate Data-transfer-and-Size-ACKnowledge (*DSACK[0:1])

BUS MASTER:
(10) If all operand byte(s) not received, recompute Address and Size and return to (1)
(11) Otherwise, operand cycle complete Assume now that the CPU 12 has requested an operand read. As in the write case, the bus controller 14 will again briefly assert the Start-OPerand-CYcle signal (SOPCY) directing the address bus interface 16 to latch the operand Address on the *IAB. Simultaneously, the bus controller 14 will negate *TRISTATE (if then asserted) to enable the address bus interface 16 to transfer the Address to the storage device 20 on the ADDRESSBUS. The bus controller 14 will also provide RW in the Read state.

A brief time later, the bus controller 14 will assert *AS to the storage device 20 indicating that a valid operand Address is on the ADDRESSBUS. Internally, the bus controller 14 will assert a Data-bus-Start-PreCHarGe signal (DSPCHG) directing the data bus interface 18 to start precharging the IDB. In addition, the bus controller 14 will pass the current operand size (*CURS[0:1]), the current low order address bits (DATAADD[0:1]), and the current direction of operand transfer (*CURRW;CURRW) to the data bus interface 18.

Upon receiving *AS, the storage device 20 will decode the address on the ADDRESSBUS. If the address is determined to be within the address range for that particular storage device 20, the storage device 20 will provide on the DATABUS as much of the requested operand as possible for the port size of that particular storage device 20. The storage device 20 will then provide *DSACK to indicate that the requested operand (or at least a portion thereof) is available on the DATABUS. As explained above, the *DSACK signal also indicates the size of the data port of that particular storage device 20.

Depending upon the size of the port (*IDSACK[0:1]), the current operand size (*CURS[0:1]) and address (DATADDD[0:1]), the data bus interface 18 can determine which bytes (E[0:3]) of the DATABUS are valid, as follows:

| IDSACK | | CURS | | DATAADD | | | valid E bytes | | | |
|---|---|---|---|---|---|---|---|---|---|---|
| 1 | 0 | 1 | 0 | 1 | 0 | RW | 0 | 1 | 2 | 3 |
| x | x | x | x | x | x | 0 | 0 | 0 | 0 | 0 |
| x | x | 0 | 1 | 0 | 0 | 1 | 1 | 0 | 0 | 0 |
| 0 | x | 0 | 1 | 0 | 1 | 1 | 1 | 0 | 0 | 0 |
| 1 | x | 0 | 1 | 0 | 1 | 1 | 0 | 1 | 0 | 0 |

-continued

| IDSACK | CURS | DATAADD | RW | valid E bytes | | | |
|---|---|---|---|---|---|---|---|
| 1 0 | 1 0 | 1 0 | | 0 | 1 | 2 | 3 |
| 0 x | 0 1 | 1 0 | 1 | 1 | 0 | 0 | 0 |
| 1 0 | 0 1 | 1 0 | 1 | 1 | 0 | 0 | 0 |
| 1 1 | 0 1 | 1 0 | 1 | 0 | 0 | 1 | 0 |
| 0 x | 0 1 | 1 1 | 1 | 1 | 0 | 0 | 0 |
| 1 0 | 0 1 | 1 1 | 1 | 0 | 1 | 0 | 0 |
| 1 1 | 0 1 | 1 1 | 1 | 0 | 0 | 0 | 1 |
| x x | 1 0 | 0 0 | 1 | 1 | 1 | 0 | 0 |
| 0 x | 1 0 | 1 0 | 1 | 1 | x | 0 | 0 |
| 1 0 | 1 0 | 1 0 | 1 | 1 | 1 | 0 | 0 |
| 1 1 | 1 0 | 1 0 | 1 | 0 | 0 | 1 | 1 |
| 0 x | 1 0 | 0 1 | 1 | 1 | 0 | x | 0 |
| 1 x | 1 0 | 0 1 | 1 | 0 | 1 | 1 | 0 |
| 0 x | 1 0 | 1 1 | 1 | 1 | 0 | x | 0 |
| 1 0 | 1 0 | 1 1 | 1 | 0 | 1 | x | 0 |
| 1 1 | 1 0 | 1 1 | 1 | 0 | 0 | x | 1 |
| x x | 0 0 | 0 0 | 1 | 1 | 1 | 1 | 1 |
| 0 x | 0 0 | 0 1 | 1 | 1 | 0 | x | x |
| 1 x | 0 0 | 0 1 | 1 | 0 | 1 | 1 | 1 |
| 0 x | 0 0 | 1 0 | 1 | 1 | x | 0 | 0 |
| 1 0 | 0 0 | 1 0 | 1 | 1 | 1 | 0 | 0 |
| 1 1 | 0 0 | 1 0 | 1 | 0 | 0 | 1 | 1 |
| 0 x | 0 0 | 1 1 | 1 | 1 | 0 | x | 0 |
| 1 0 | 0 0 | 1 1 | 1 | 0 | 1 | x | 0 |
| 1 1 | 0 0 | 1 1 | 1 | 0 | 0 | x | 1 |
| 0 x | 1 1 | 0 1 | 1 | 1 | 0 | x | x |
| 1 x | 1 1 | 0 1 | 1 | 0 | 1 | 1 | 1 |
| 0 x | 1 1 | 1 0 | 1 | 1 | x | 0 | 0 |
| 1 0 | 1 1 | 1 0 | 1 | 1 | 1 | 0 | 0 |
| 1 1 | 1 1 | 1 0 | 1 | 0 | 0 | 1 | 1 |
| 0 x | 1 1 | 1 1 | 1 | 1 | 0 | x | 0 |
| 1 0 | 1 1 | 1 1 | 1 | 0 | 1 | x | 0 |
| 1 1 | 1 1 | 1 1 | 1 | 0 | 0 | x | 1 |
| x x | 1 1 | 0 0 | 1 | 1 | 1 | 1 | x | where: x= >don't care.

Depending upon the current operand size (*CURS[0:1]) and the current operand address (DATAADD[0:1]), the data bus interface 18 will couple the valid byte(s) on the DATABUS to the proper byte(s) of the IDB as described above. Using just the current operand size (S[0:1]), the bus controller 14 can then provide a Data-Bus-INput:Latch-Byte signal (DBINLB[0:3]) indicating which bytes (I[0:3]) of the IDB are valid, as follows:

| S1 | S0 | I0 | I1 | I2 | I3 |
|---|---|---|---|---|---|
| 0 | 0 | 1 | 1 | 1 | 1 |
| 0 | 1 | 0 | 0 | 0 | 1 |
| 1 | 0 | 0 | 0 | 1 | 1 |
| 1 | 1 | 0 | 1 | 1 | 1 |

In response to DBINLB signal, the CPU 12 will latch the valid bytes provided by the data bus interface 18 on the IDB into the appropriate destination register (not shown).

Using the current operand size (S[0:1]) and address (*CURAD[0:1]) and the size of the port (*DSACK[0:1]), the bus controller 14 can determine how much of the requested operand remains to be provided by the storage device 20, in a similar manner to that described above in the write case. Thus, for example, if the port size of the storage device 20 is the same as the size of the DATABUS or if the size of the operand is less than or equal to the port size of the storage device 20, the bus controller 14 will know that all of the operand has been received and that the operand cycle can be terminated. In this event, the bus controller 14 will terminate the bus cycle by negating *AS and *DS. Simultaneously, the bus controller 14 will assert *TSDB to force the data bus interface 18 to decouple from the DATABUS. The bus controller 14 will also remove DBINLB and then assert OPCYCOM to advise the CPU 12 that the requested operand read has been completed. A brief time latter, if another bus master (not shown) has requested the use of the communication bus, the bus controller 14 will assert *TRISTATE to force the address bus interface 16 to remove the address from the ADDRESSBUS. In response to the negation of *AS and *DS, the storage device 20 will withdraw the operand byte(s) from the DATABUS, and then terminate *DSACK. At this time, the communication bus again becomes available for use by the CPU 12 or any other bus master (not shown) which may be present in the system.

If additional bus cycles are required to complete the operand cycle, the bus controller 14 will recompute the two low order bits A0 and A1 of the address of the residual operand as described above. The bus controller 14 will then provide the address bus interface 16 with the new low order address bits A0 and A1 (NXTA[0:1]). If the communication bus has been used by another bus master (not shown) since the previous bus cycle of the current operand cycle, the bus controller 14 will assert ARESTORE requesting the address bus interface to restore the original higher order address bits (*IAD[2:31]), but use the two new low order address bits (NXTA[0:1]). On the other hand, if the new address bits have rolled over, the bus controller 14 will assert INCA2A31 requesting the address bus interface 16 to increment the original higher order address bits (*IAD[2:31]), and use the resultant address together with the two new low order address bits (NXTA[0:1]). As indicated before, the address bus interface 16 has already incremented the higher order address bits A2–A31 in anticipation of this request. Thus, the bus controller 14 can immediately assert (SNXTBC) requesting the address bus interface 16 to start the next bus cycle using the new address. From this point on, the bus controller 14 cooperates with the address bus interface 16 and the data bus interface 18 as described above. If necessary, this sequence is repeated until all of the requested operand has been received and latched into the CPU 12.

In general, the read cycle can be summarized with respect to any bus master reading an operand from a bus slave as follows:

BUS MASTER:
 (1) Set Read/Write to Read
 (2) Drive address on ADDRESSBUS
 (3) Drive Size (S[0:1])
 (4) Assert Address-Strobe (*AS)
 (5) Assert Data-Strobe (*DS)
BUS SLAVE:
 (1) Decode address on ADDRESSBUS
 (2) Drive operand byte(s) on DATABUS
 (3) Assert Data-transfer-and-Size-ACKnowledge (*DSACK[0:1])
BUS MASTER:
 (6) Latch operand byte(s) into register
 (7) Negate Data-Strobe (*DS)
 (8) Negate Address-Strobe (*AS)
BUS SLAVE
 (4) Remove operand byte(s) from DATABUS
 (5) Negate Data-transfer-and-Size-ACKnowledge (*DSACK[0:1])
BUS MASTER:

(9) If all operand byte(s) not received, recompute Address and Size and return to (1)

(10) Otherwise, operand cycle complete

Figure 2:
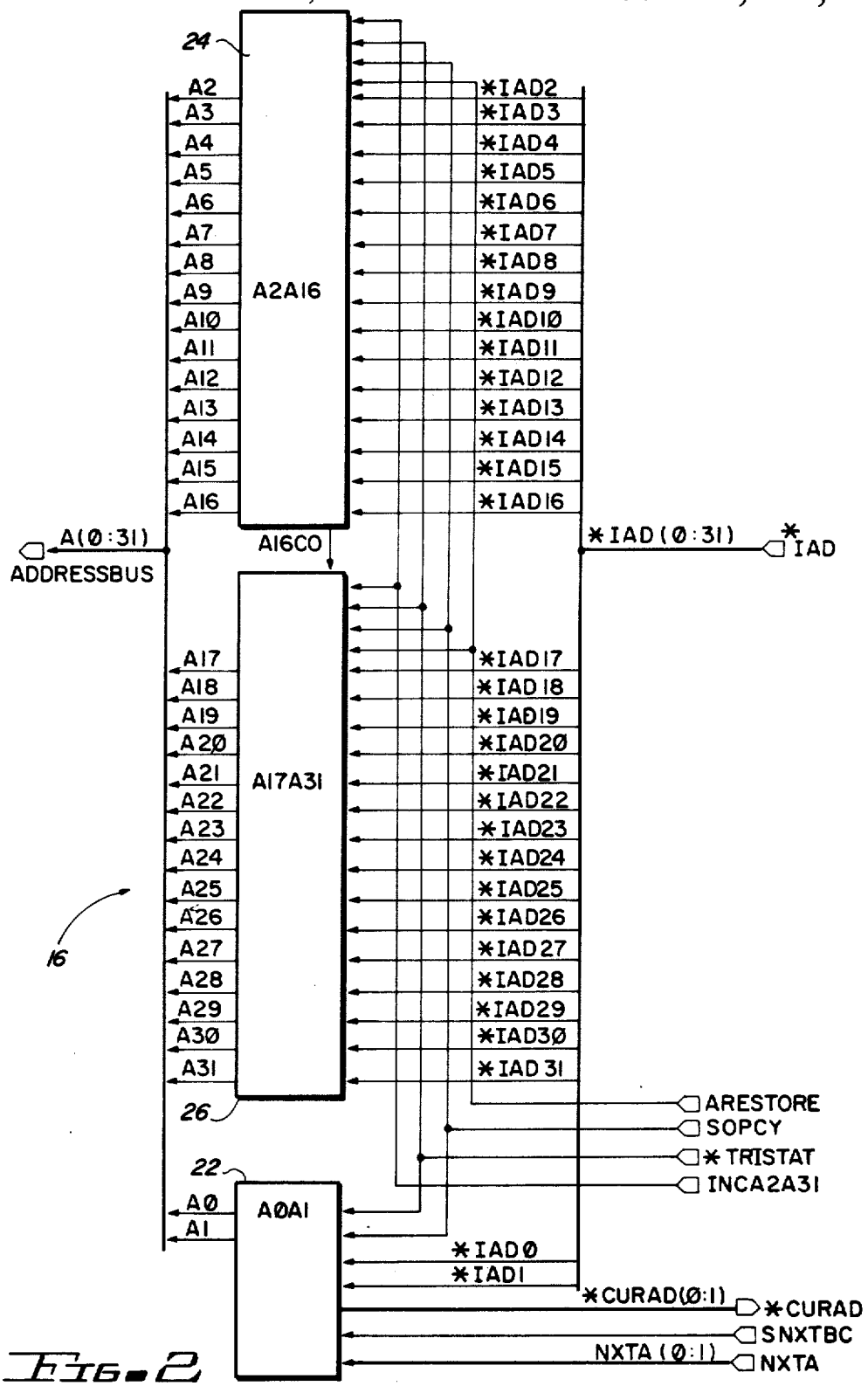
FIG. 2 is a block diagram of the address bus interface of the data processor of FIG. 1.
Figure 5:
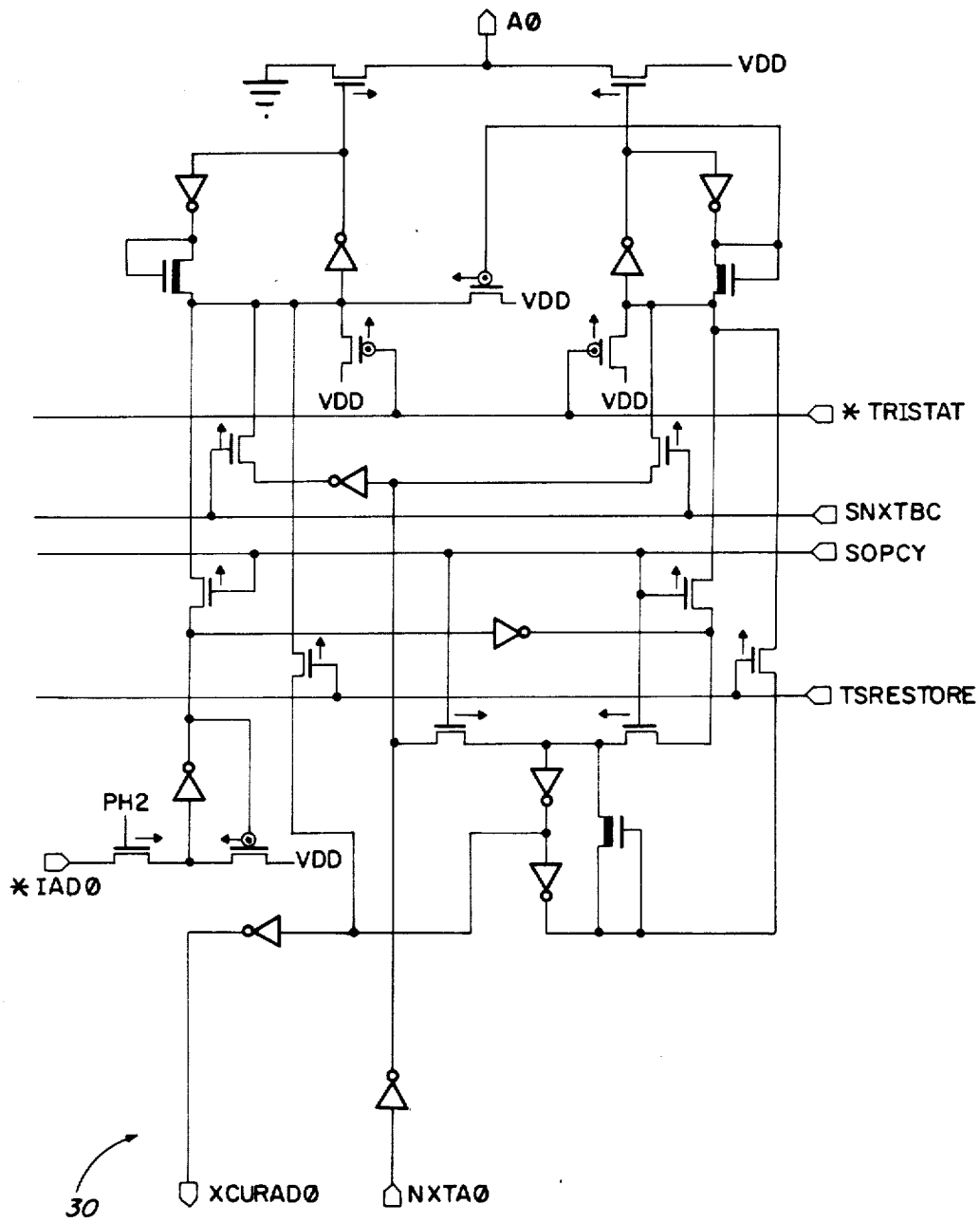
FIG. 5 is a detailed schematic of the A0 interface of FIG. 3, the A1 interface being identical.
Figure 6:
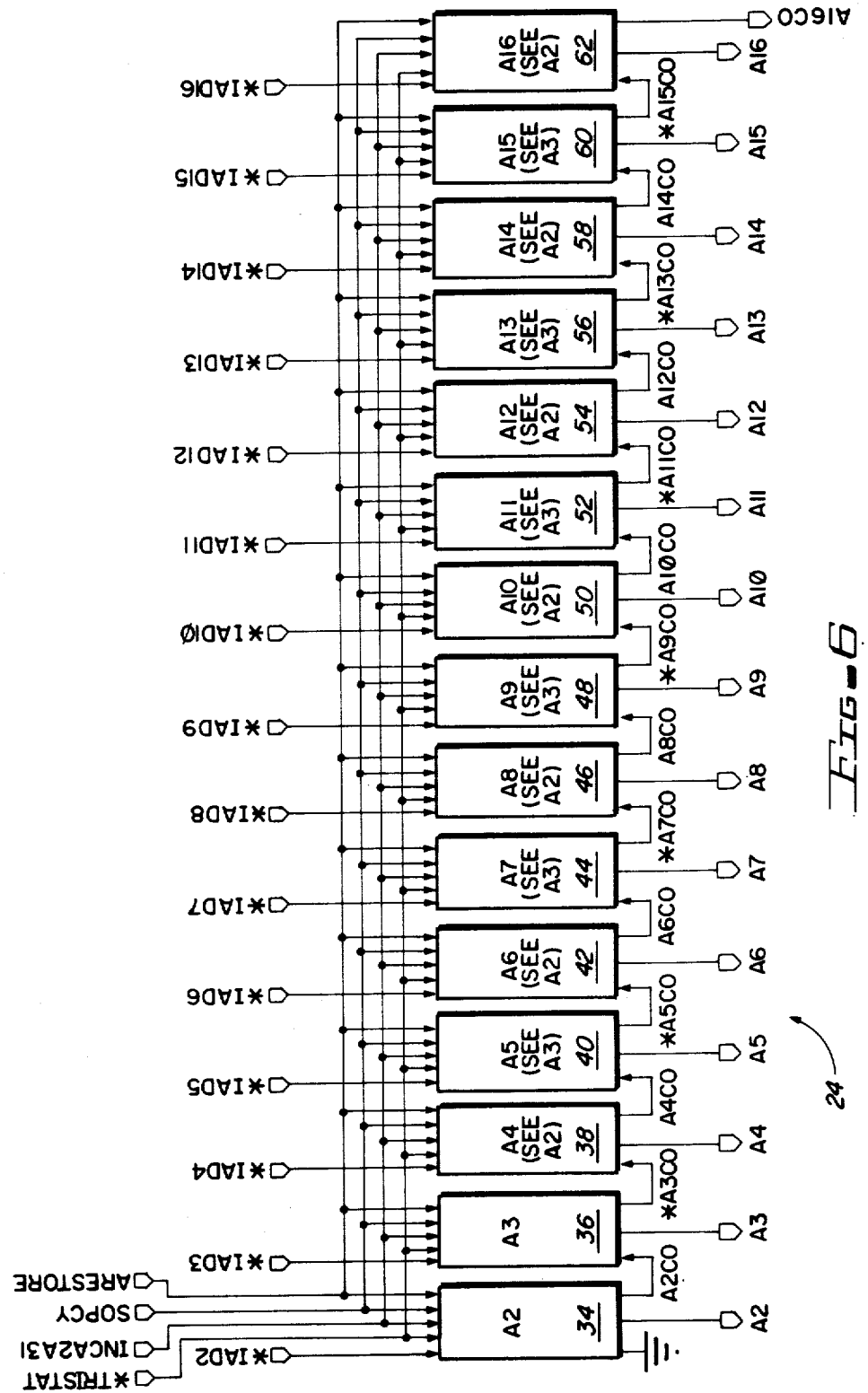
FIG. 6 is a block diagram of the A2 through A16 interfaces of the address bus interface of FIG. 2.
Figure 7:
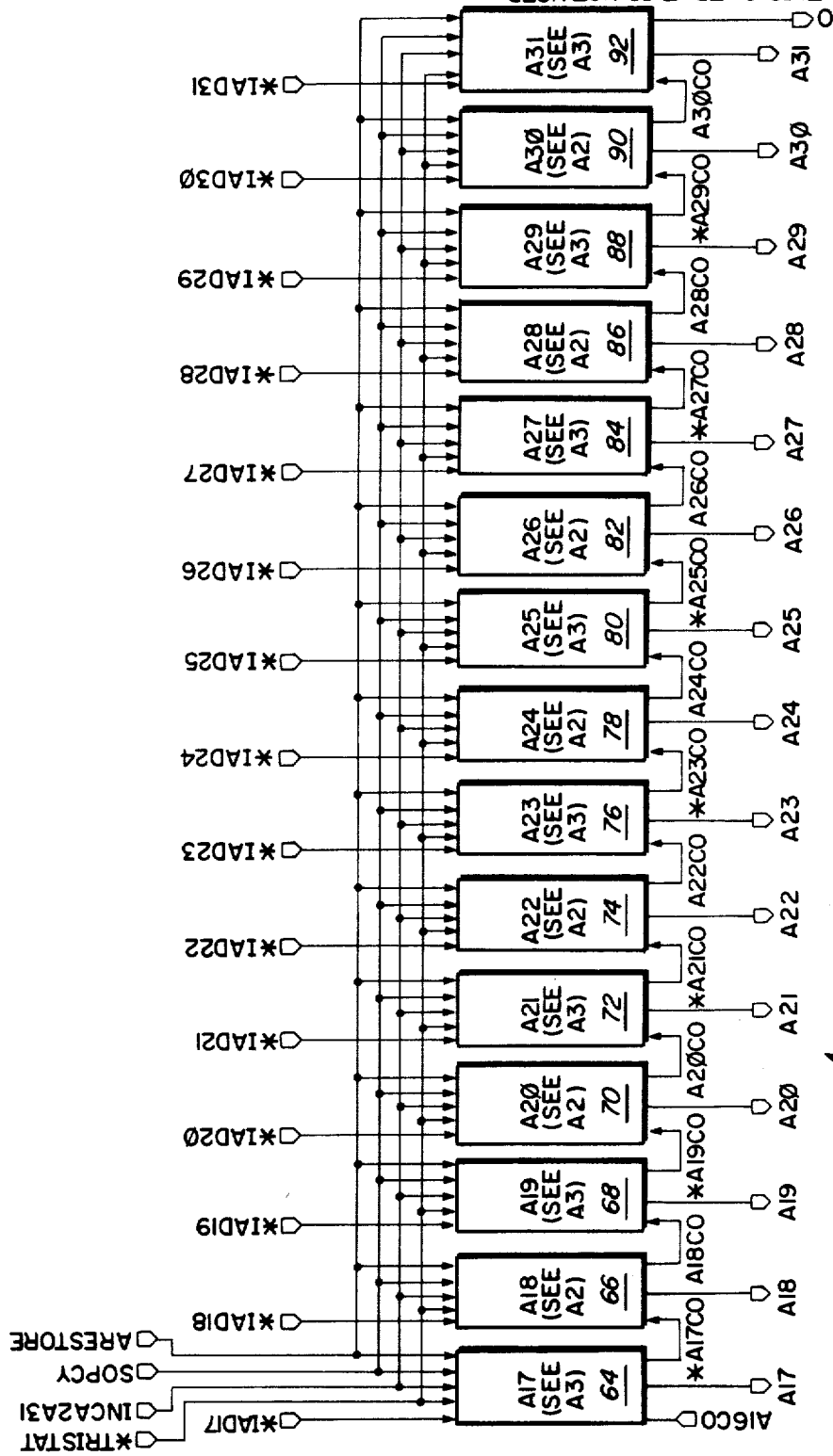
FIG. 7 is a block diagram of the A17 through A32 interfaces of the address bus interface of FIG. 2.
Figure 8:
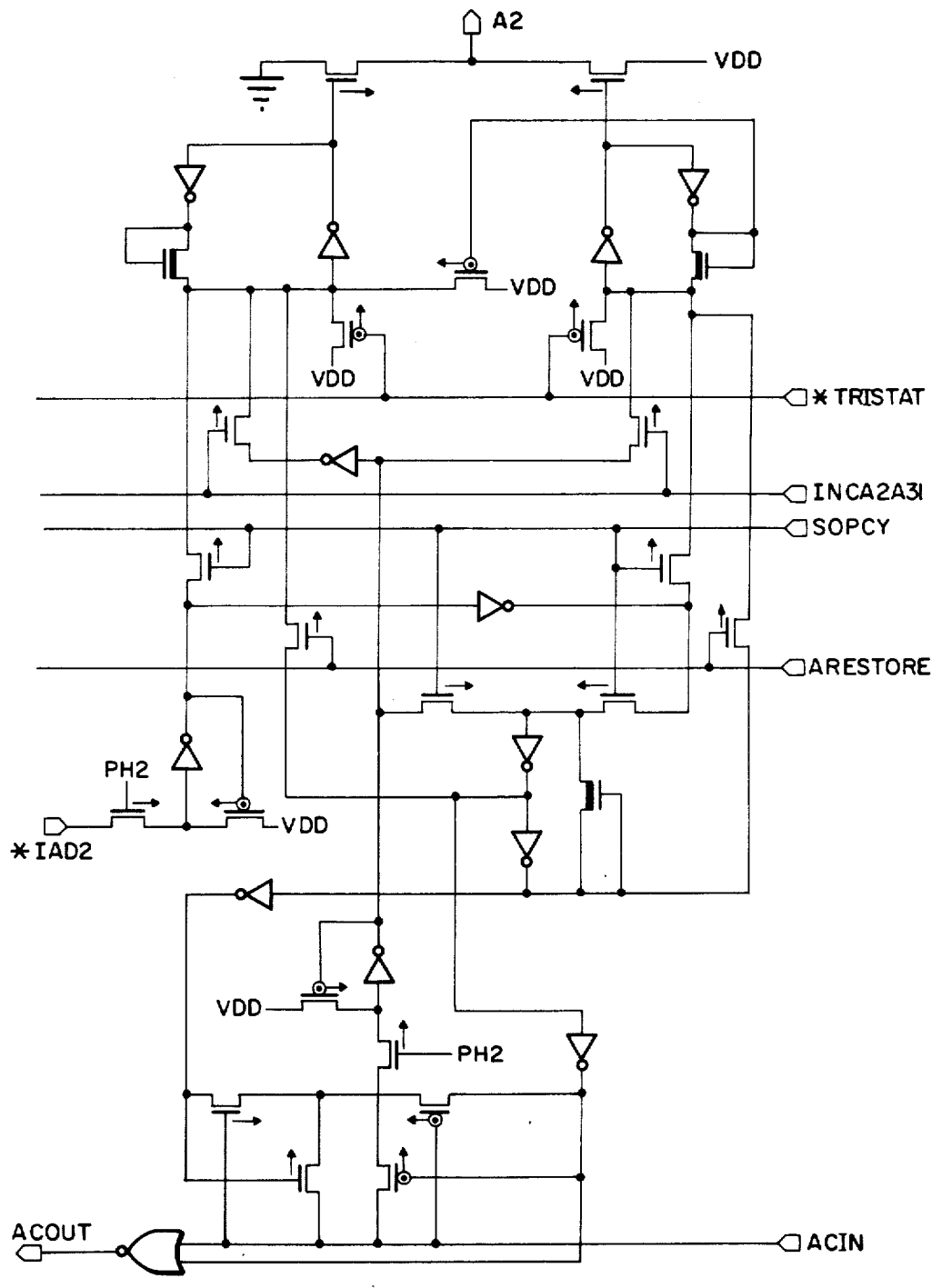
FIG. 8 is a detailed schematic of the A2 interface of FIG. 6, the A4, A6, A8, A10, A12, A14, A16, A18, A20, A22, A24, A26, A28, A30 and A32 interfaces being identical.
Figure 9:
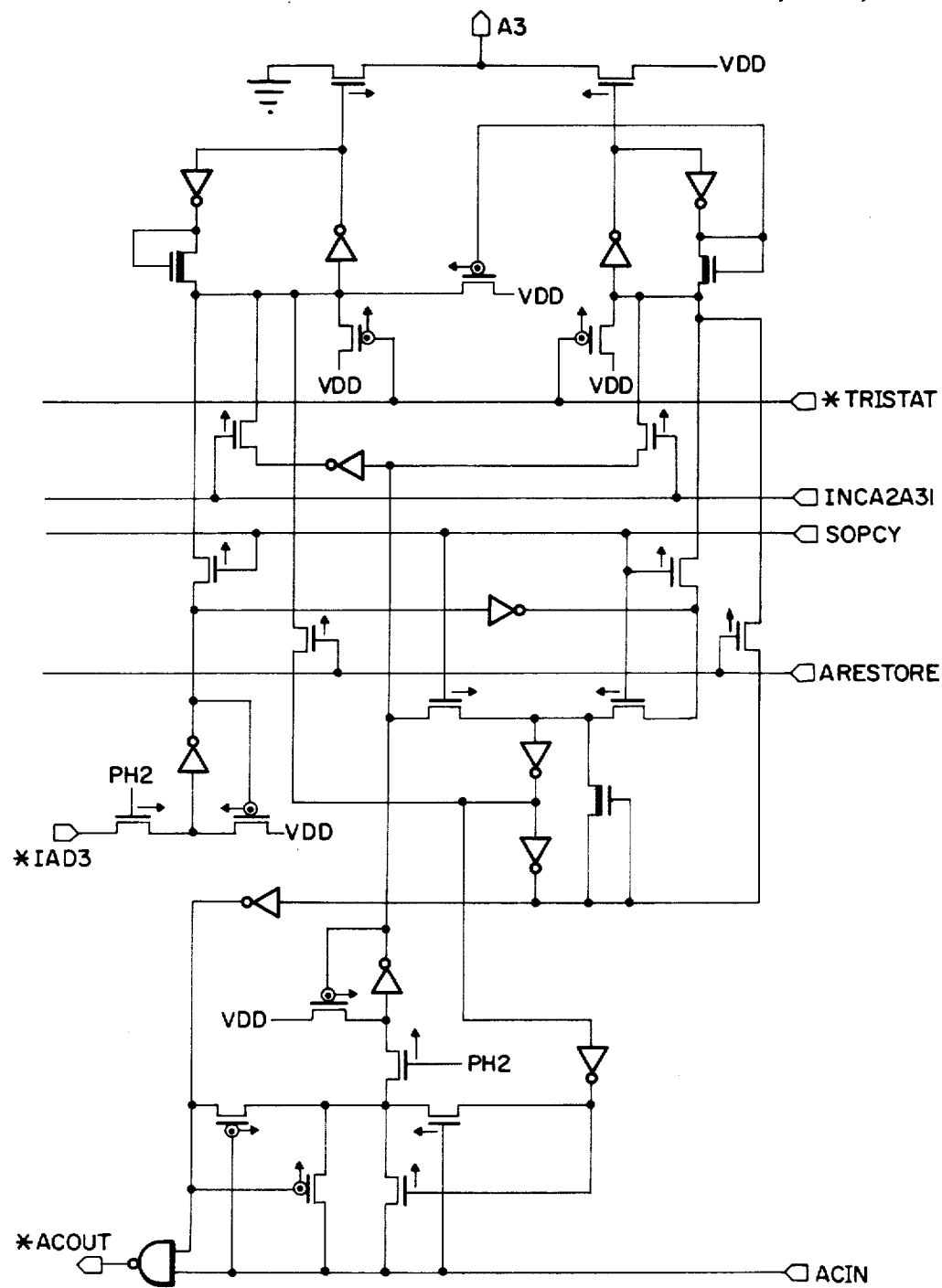
FIG. 9 is a detailed schematic of the A3 interface of FIG. 6, the A5, A7, A9, A11, A13, A15, A17, A19, A21, A23, A25, A27, A29 and A31 interfaces being identical.

As shown in FIG. 2, the preferred embodiment of the address bus interface 16 is comprised of an A0A1 interface 22, an A2A16 interface 24, and an A17A31 interface 26. As can be seen in FIG. 3, the A0A1 interface 22 is comprised of an ADDress RESTore 28, an A0 interface 30 and an A1 interface 32 which is identical to the A0 interface 30. Detailed schematic diagrams of the ADDREST 28 and the A0 interface 30 are shonw in FIGS. 4 and 5, respectively. As shown in FIG. 6, the A2A16 interface 24 is comprised of A2 through A16 interfaces 34 through 62, respectively. Similarly, the A17A31 interface 26 is comprised of A17 through A31 interfaces 64 through 92, respectively. A detailed schematic diagram is shown in FIG. 8 of the A2 interface 34, the A4, A6, A8, A10, A12, A14, A16, A18, A20, A22, A24, A26, A28, and A30 interfaces 38, 42, 46, 50, 54, 58, 62, 66, 70, 74, 78, 82, 86 and 90, respectively, being identical. Similarly, a detailed schematic diagram is shown in FIG. 9 of the A3 interface 36, and A5, A7, A9, A11, A13, A15, A17, A19, A21, A23, A25, A27, A29, and A31 interfaces 40, 44, 48, 52, 56, 60, 64, 68, 72, 76, 80, 84, 88 and 92, respectively, being identical.

Figure 10:
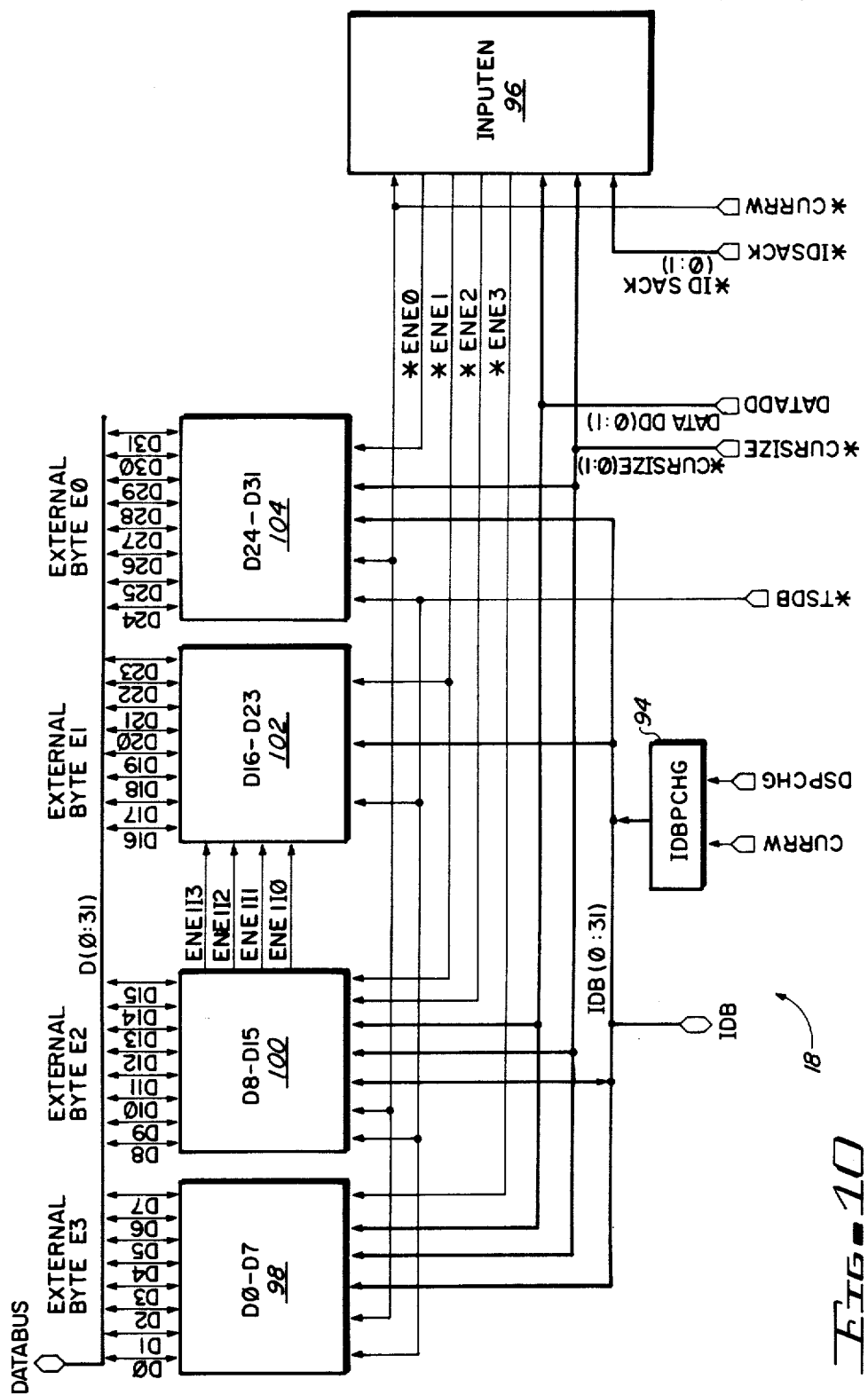
FIG. 10 is a block diagram of the data bus interface of the data processor of FIG. 1.
Figure 11:
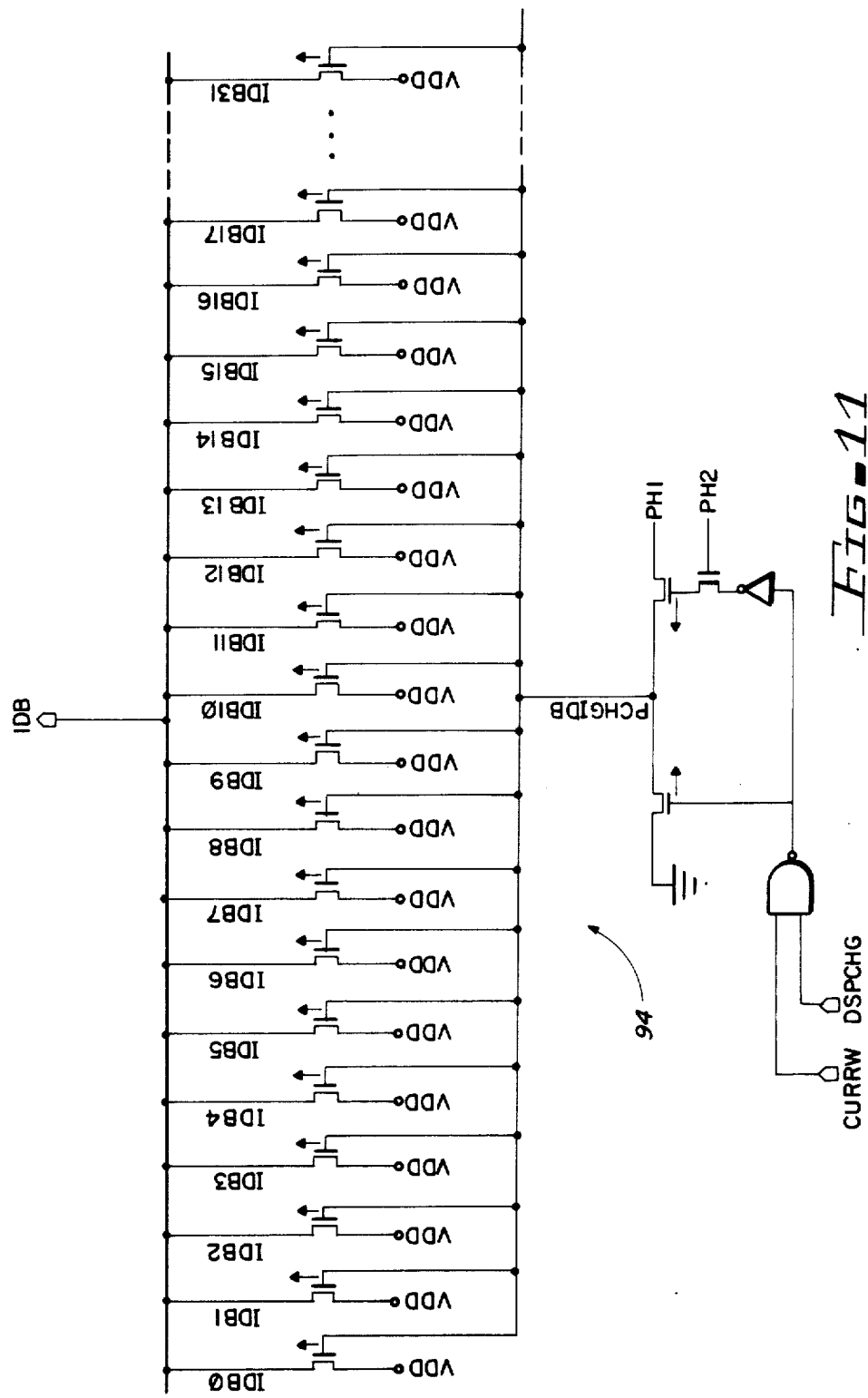
FIG. 11 is a detailed schematic diagram of the internal data bus precharge portion of the data bus interface of FIG. 10.
Figure 14:
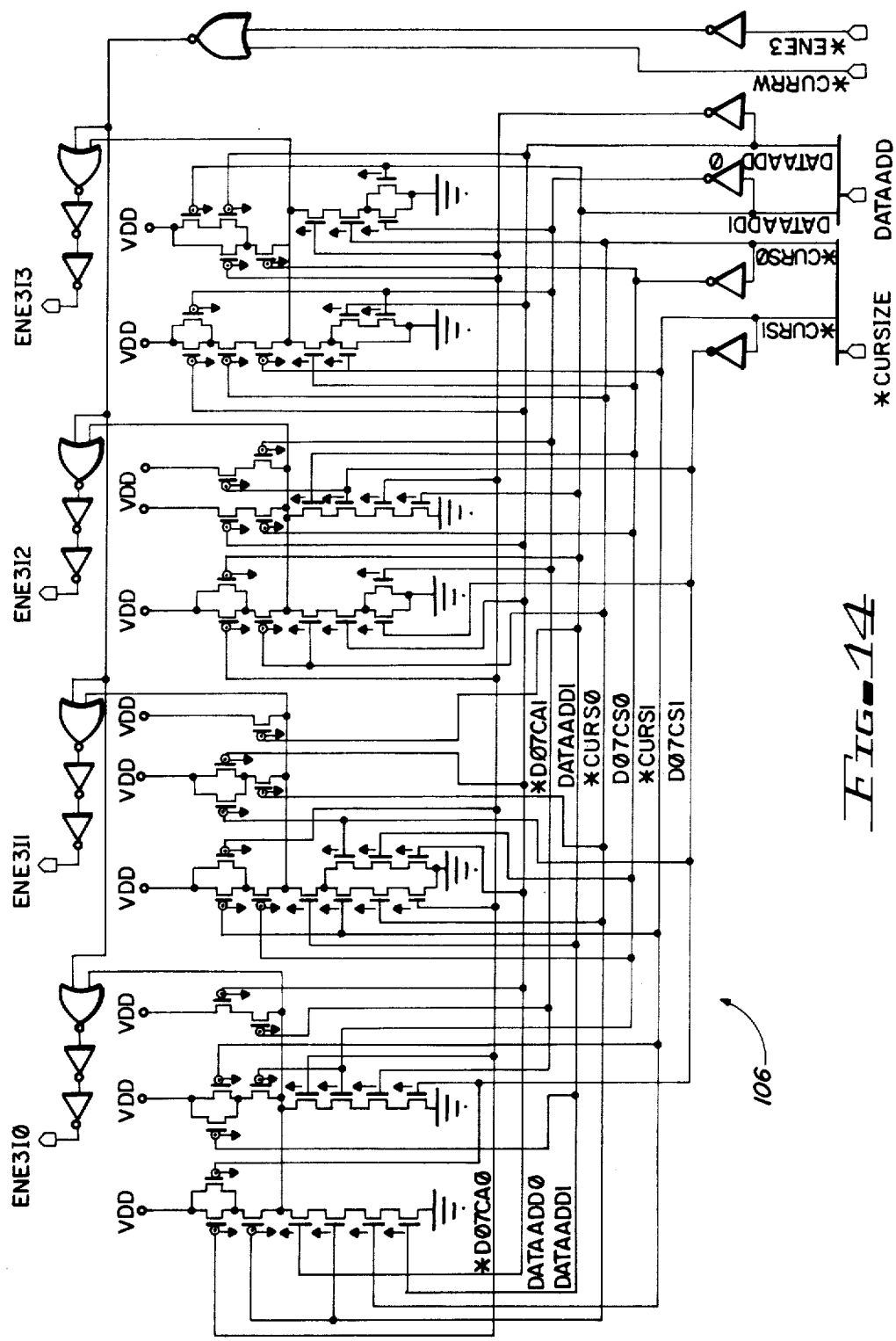
FIG. 14 is a detailed schematic diagram of the control for the D0–D7 interfaces of FIG. 13.
Figure 15:
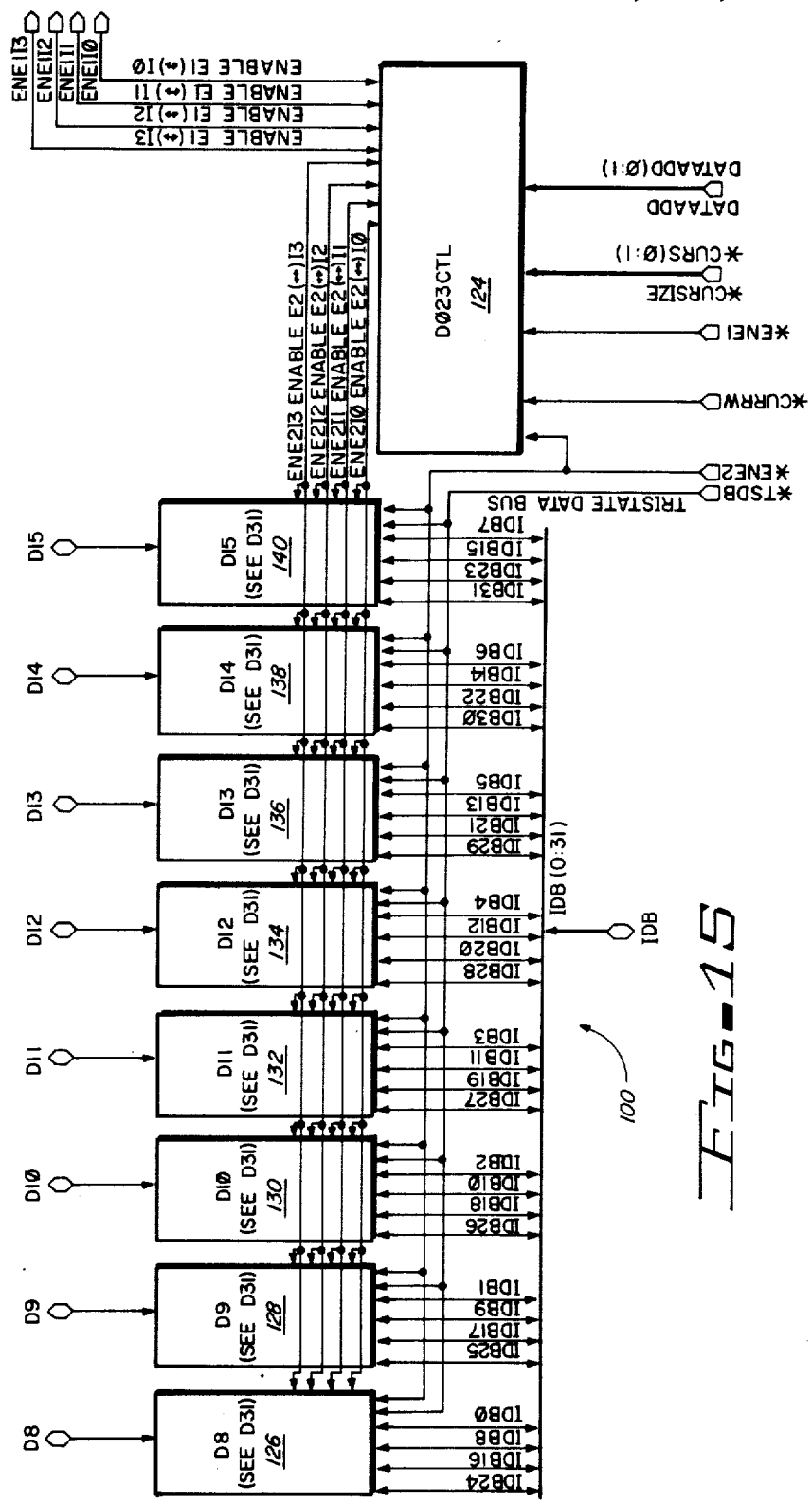
FIG. 15 is a block diagram of the D8 through D15 interfaces of the data bus interface of FIG. 10.
Figure 17:
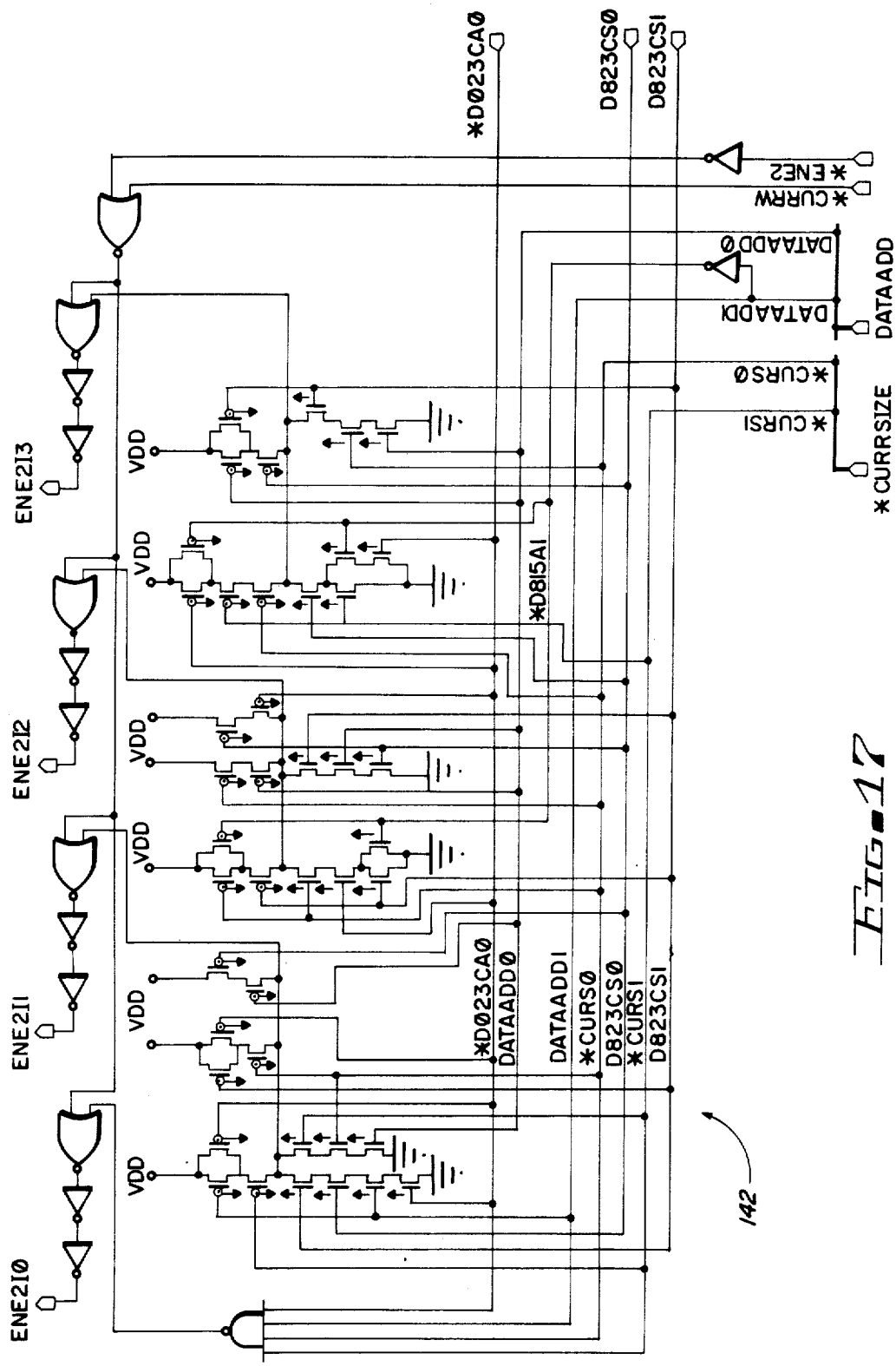
FIG. 17 is a detailed schematic diagram of the control for the D8–D15 interfaces of the data bus interface of FIG. 16.
Figure 16:
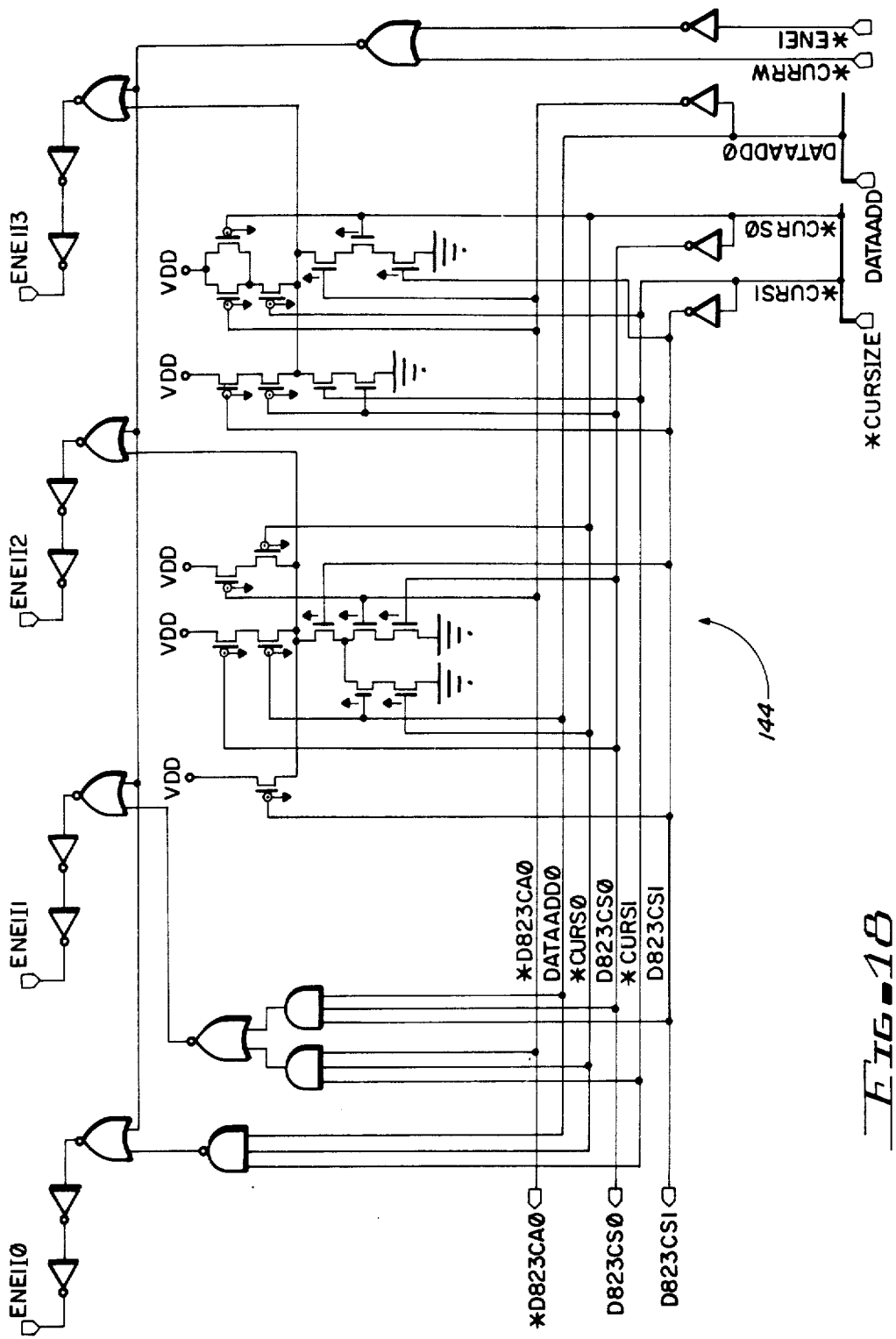
FIG. 16 is a block diagram of the control for the D8–D23 interfaces of the data bus interface of FIG. 15.
Figure 22:
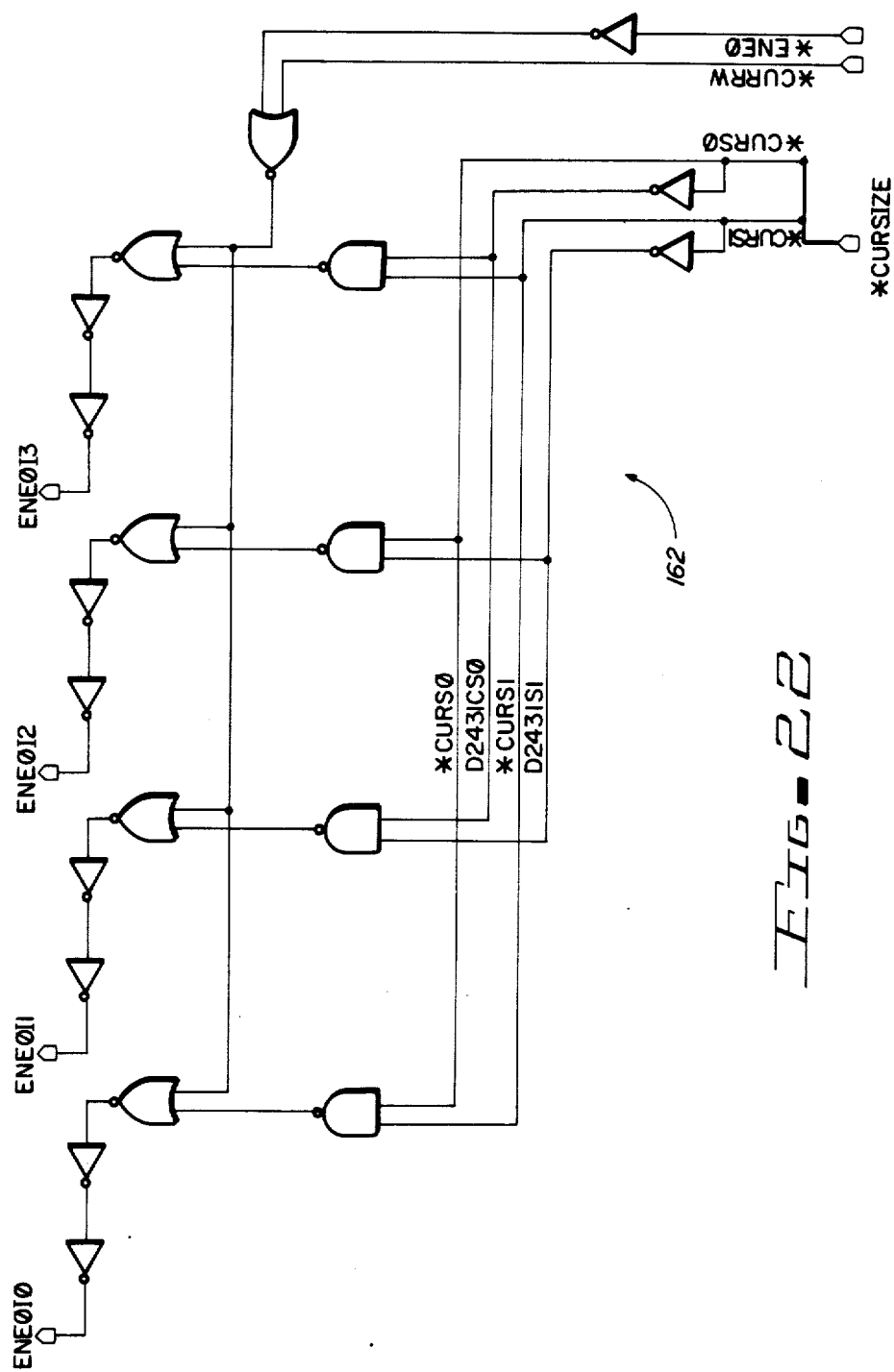
FIG. 22 is a detailed schematic diagram of the control of the D24-D31 interfaces of FIG. 20.

As shown in FIG. 10, the preferred embodiment of the data bus interface 18 is comprised of an Internal Data Bus PreCHarGe (IDBPCHG) 94, and INPUT ENable (INPUTEN) 96, a D0-D7 interface 98, a D8-D15 interface 100, a D16-D23 interface 102 and a D24-D31 interface 104. A detailed schematic diagram of the IDBPCHG 94 is shown in FIG. 11. A detailed schematic diagram of the INPUTEN 96 is shown in FIG. 12. As can be seen in FIG. 13, the D0-D7 interface 98 is comprised of a D0-D7 ConTroL (D07CTL) 106, and D0 through D7 interfaces 108 through 122, respectively. A detailed schematic diagram of the D07CTL 106 is shown in FIG. 14. As can be seen in FIG. 15, the D8-D15 interface 100 is comprised of a D8-D23 ConTroL (D823CTL) 124, and D8 through D15 interfaces 126 through 140, respectively. As shown in FIG. 16, the D823CTL 124 is comprised of a D8-D15 ConTroL (D815CTL) 142 and a D16-D23 ConTroL (D1623CTL) 144. A detailed schematic diagram of the D815CTL 142 is shown in FIG. 17. A detailed schematic diagram of the D1623CTL 144 is shown in FIG. 18. As can be seen in FIG. 19, the D16-D23 interface 102 is comprised of D16 through D23 interfaces 146 through 160, respectively. As can be seen in FIG. 20, the D24-D31 interface 104 is comprised of a D24-D31 ConTroL (D2431CTL) 162, and D24 through D31 interfaces 164 through 178, respectively. A detailed schematic diagram is shown in FIG. 21 of the D31 interface 178, the D0 through D30 interfaces 108-122, 126-140, 146-160, and 164-176, respectively, being identical. A detailed schematic diagram of the D2431CTL 162 is shown in FIG. 22.

Figure 23:
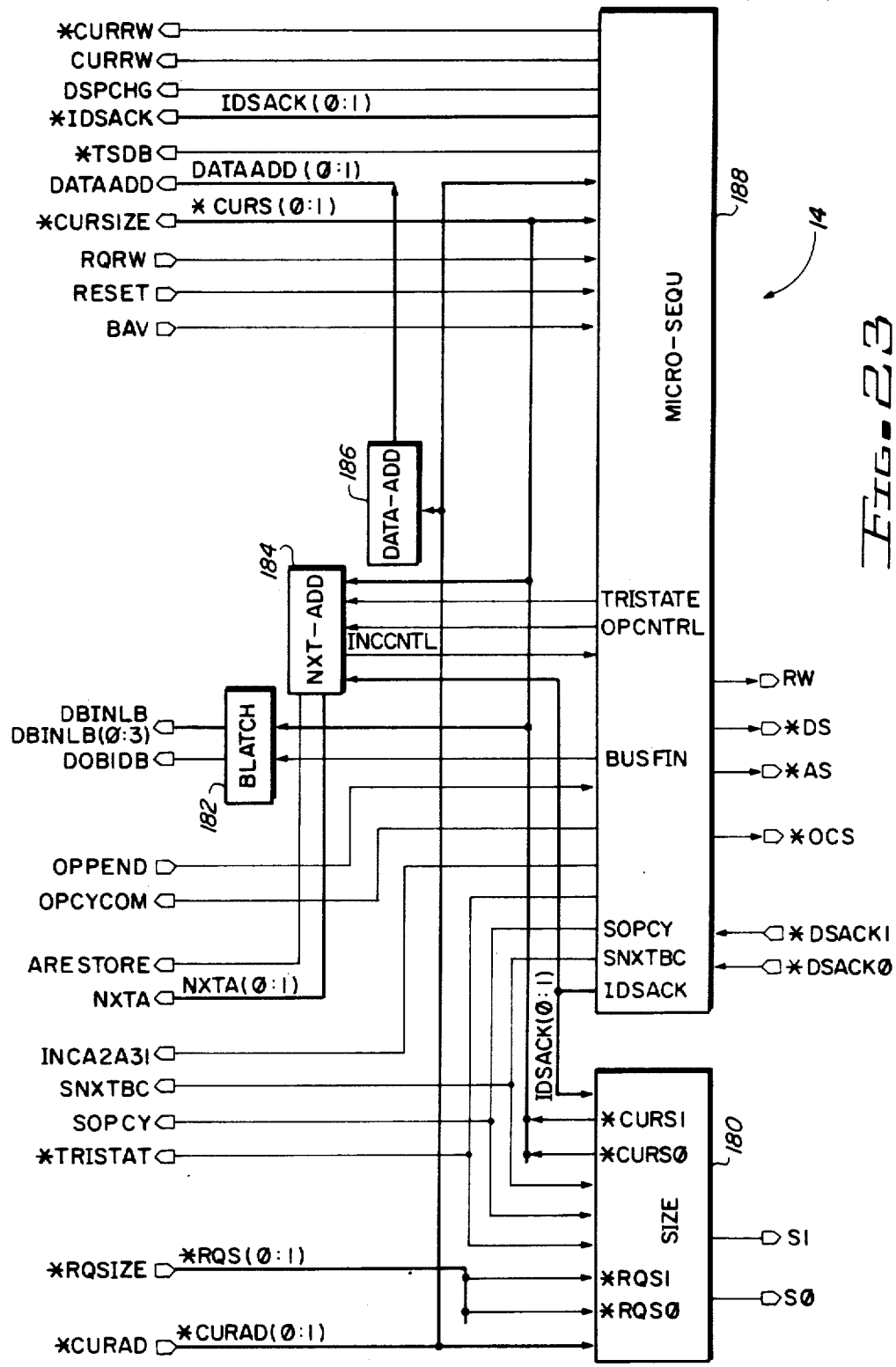
FIG. 23 is a block diagram of the bus controller of the data processor of FIG. 1.
Figure 24:
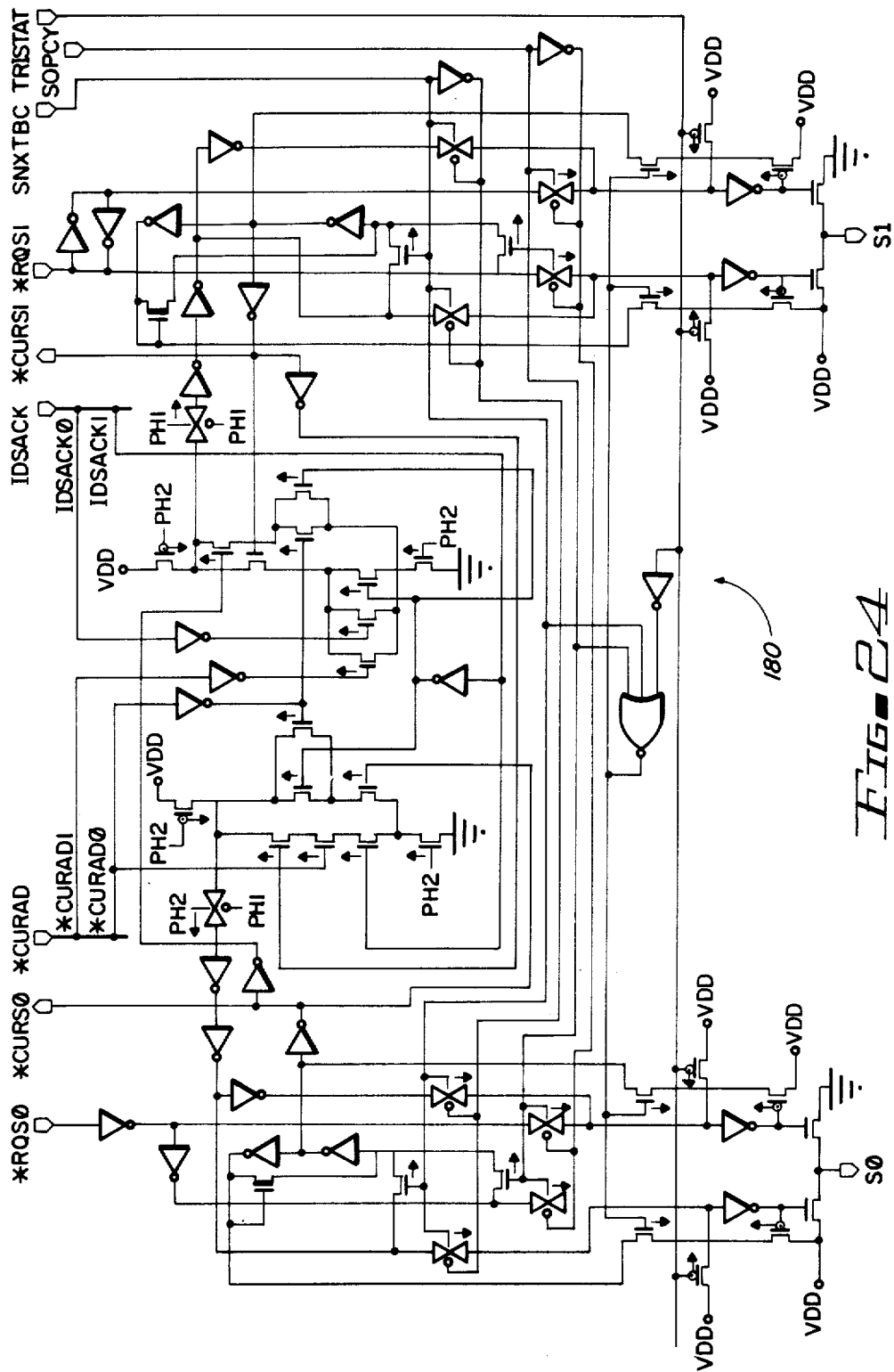
FIG. 24 is a detailed schematic diagram of the size control portion of the bus controller of FIG. 23.
Figure 25:
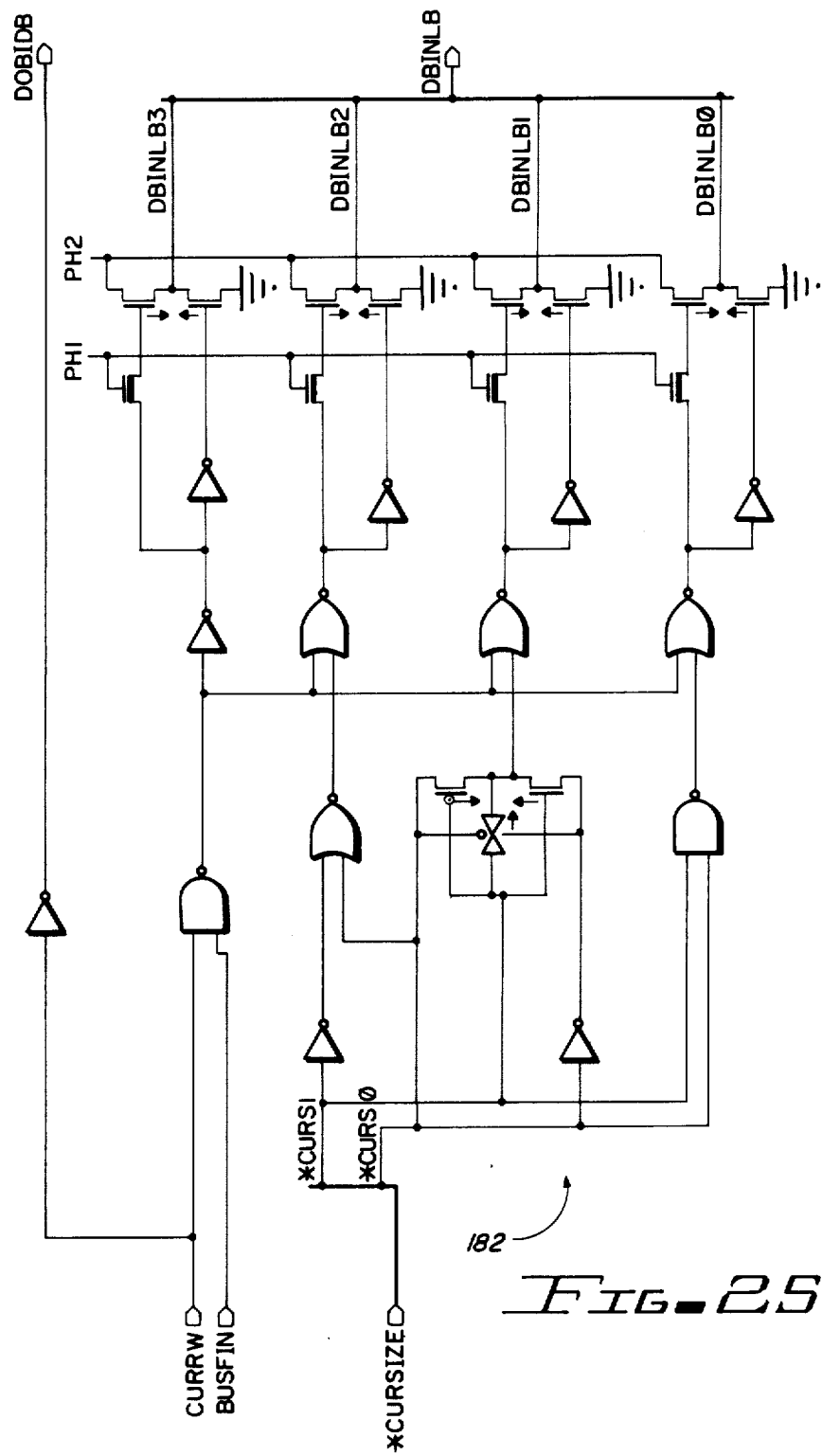
FIG. 25 is a detailed schematic diagram of the byte latch control of the bus controller of FIG. 23.
Figure 26:
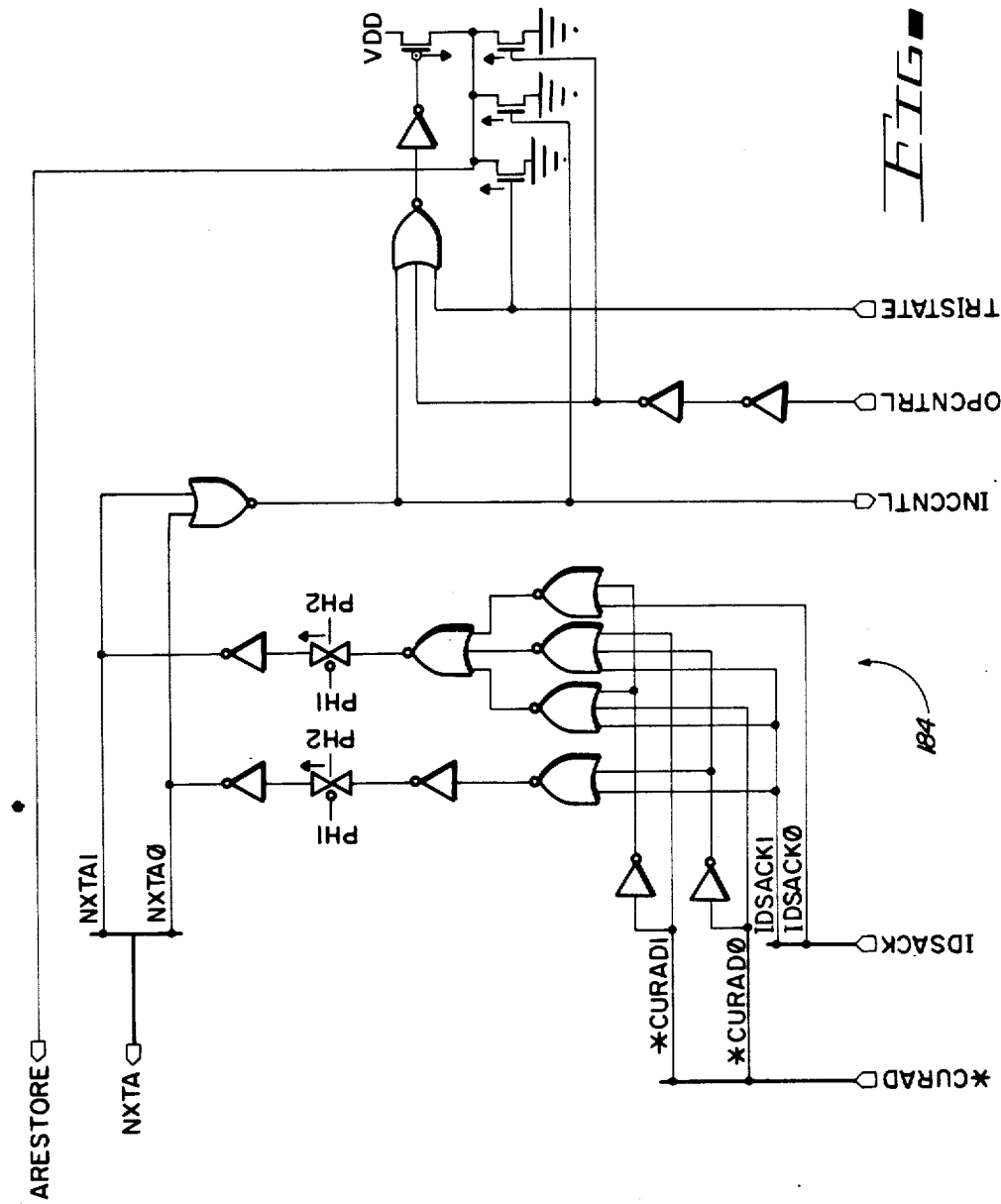
FIG. 26 is a detailed schematic diagram of the next address control of the bus controller of FIG. 23.
Figure 29:
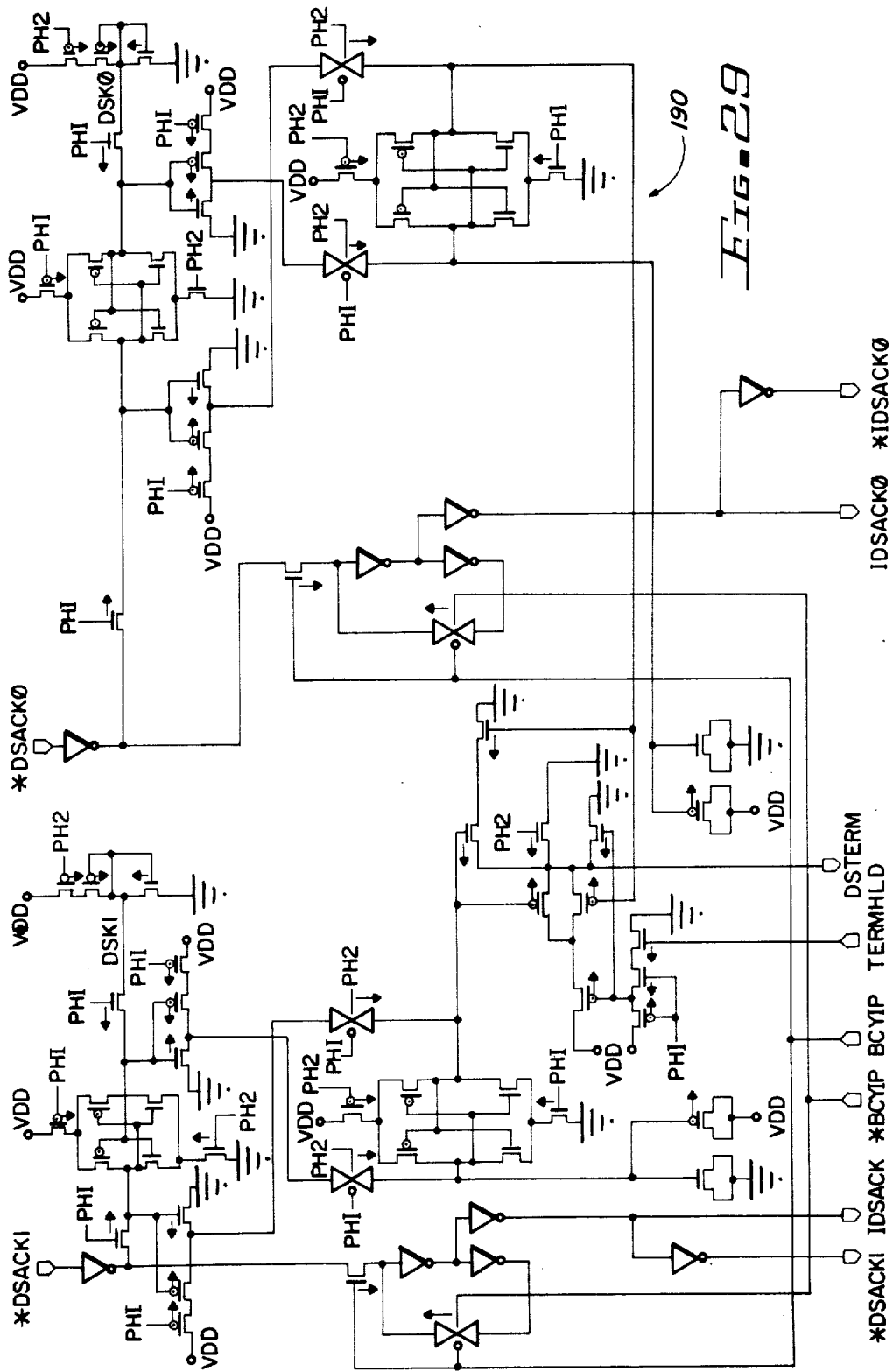
FIG. 29 is a detailed schematic diagram of the data size input synchronizer of the microsequencer of FIG. 28.
Figure 30:
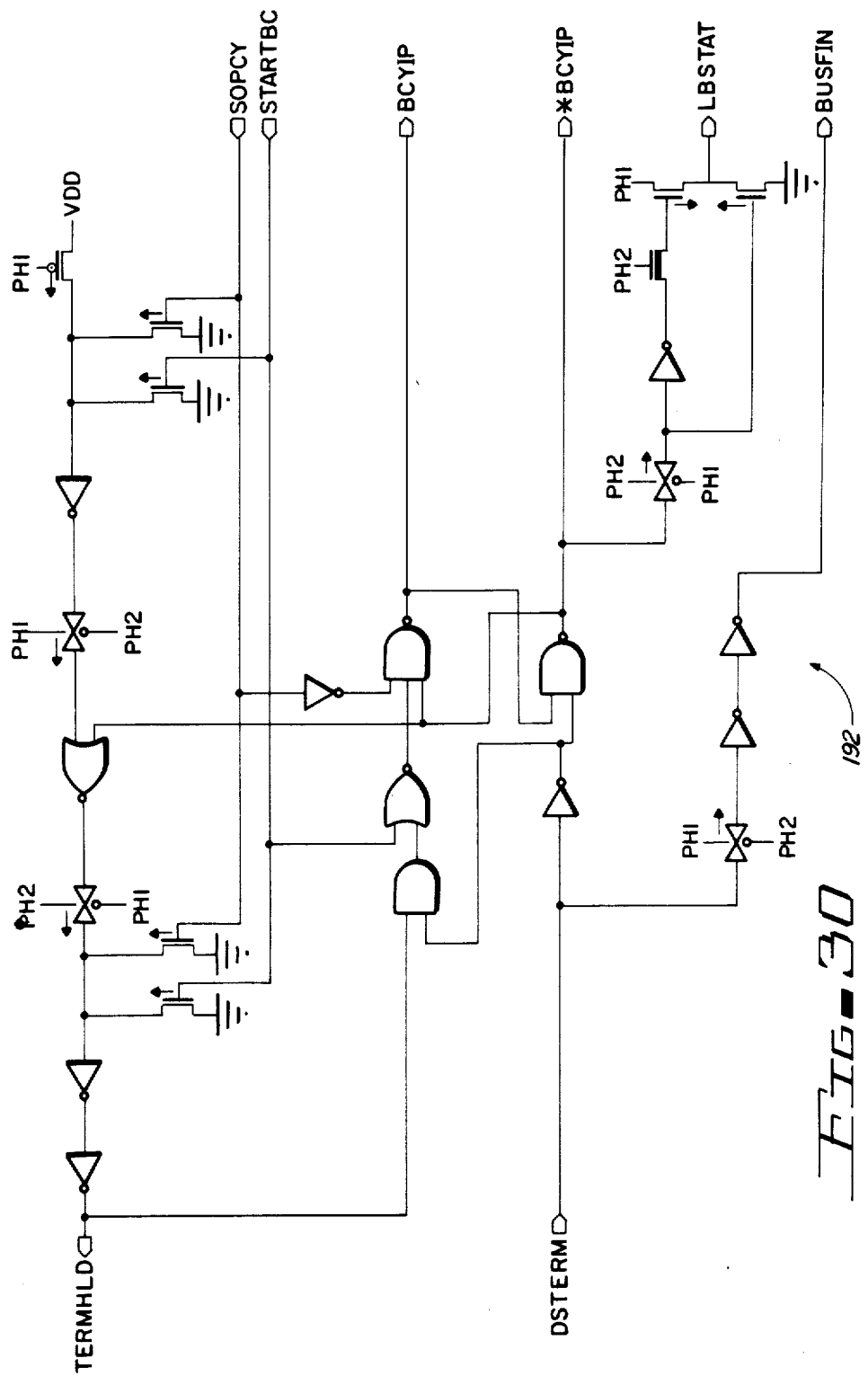
FIG. 30 is a detailed schematic diagram of the termination control of the microsequencer of FIG. 28.
Figure 31:
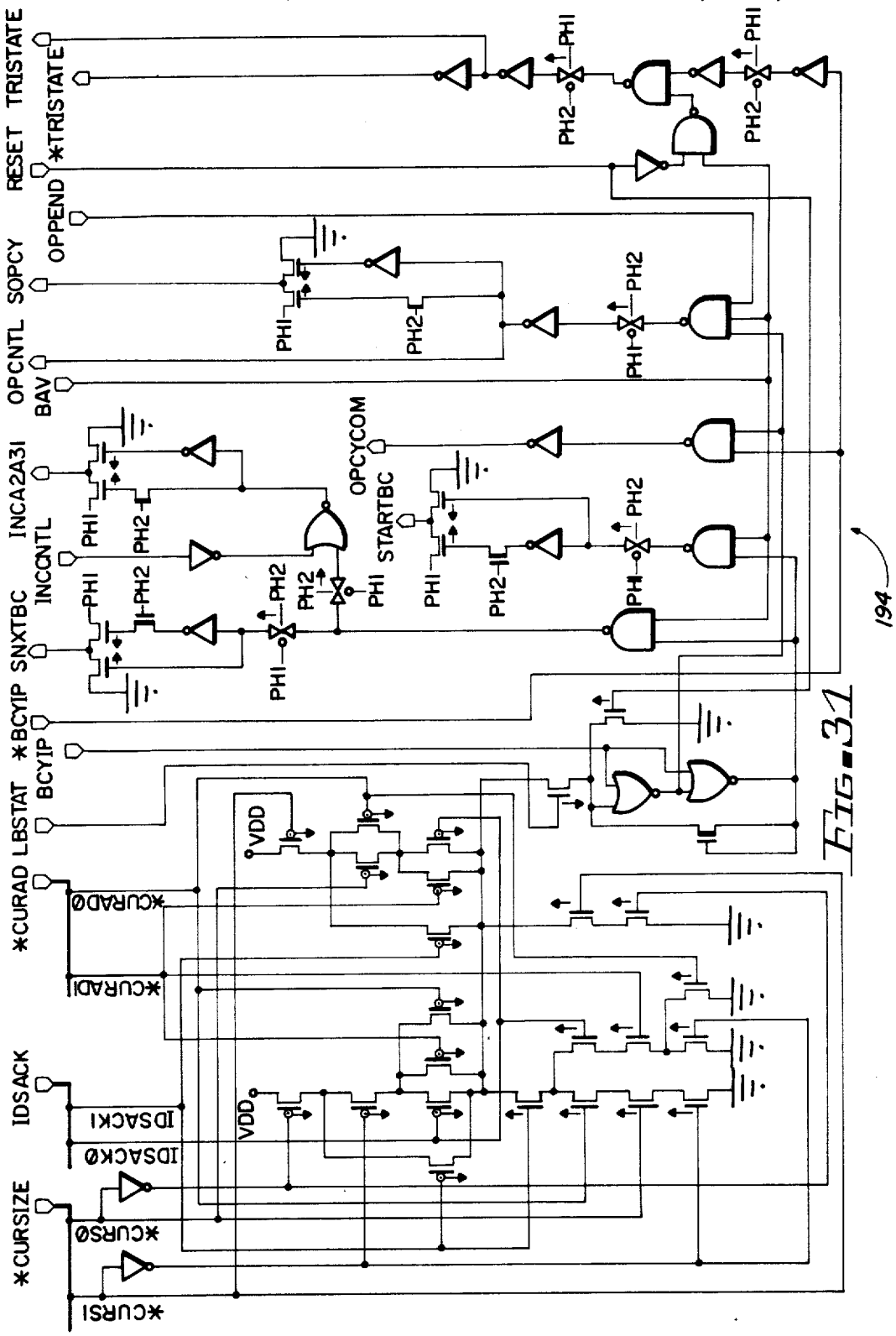
FIG. 31 is a detailed schematic diagram of the state control of the microsequencer of FIG. 28.
Figure 32:
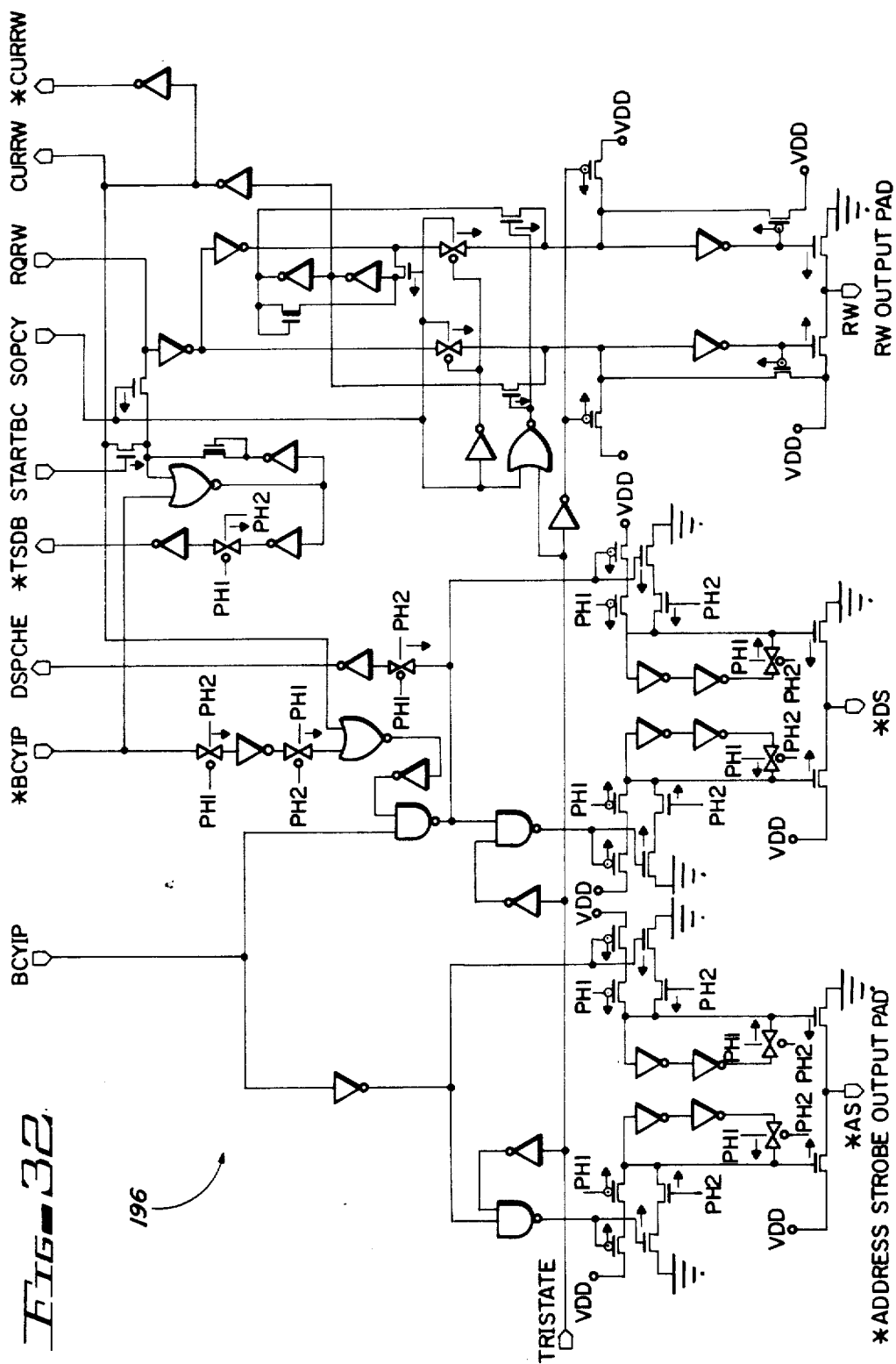
FIG. 32 is a detailed schematic diagram of the start bus cycle control of the microsequencer of FIG. 28.

As shown in FIG. 23, the bus controller 14 is comprised of a SIZE circuit (SIZE) 180, a Byte LATCH enable circuit (BLATCH) 182, a NeXT ADDress generator (NXT-ADD) 184, a DATA ADDress buffer (DATA_ADD) 186, and a MICRO SEQUencer (MICRO_SEQU) 188. A detailed schematic diagram of the SIZE circuit 180 is shown in FIG. 24. A detailed schematic diagram of the BLATCH 182 is shown in FIG. 25. A detailed schematic diagram of the NXT-ADD generator 184 is shown in FIG. 26. A detailed schematic diagram of the DATA-ADD buffer 186 is shown in FIG. 27. As can be seen in FIG. 28, the MICROSEQUencer 188 is comprised of a Data Size Input SYNCHronizer (DSISYNCH) 190, a TERMination ConTrol 192, a STATe ConTroL 194, and a STroBe Bus Cycle control (STBBC) 196. A detailed schematic diagram of the DSISYNCH 190 is shown in FIG. 29. A detailed schematic diagram of the TERMCTL 192 is shown in FIG. 30. A detailed schematic diagram of the STATCTL 194 is shown in FIG. 31. A detailed schematic diagram of the STBBC 196 is shown in FIG. 32.

As will be clear to those skilled in the art, the CPU 12 may take any of a number of well known forms. For example, the CPU 12 may be constructed along the lines of that described in U.S. Pat. No. 4,325,121. On the other hand, the bus controller 14, address bus interface 16 and data bus interface 18 may be readily adapted to perform operand cycles for any of the other well known forms of bus master such as direct memory access controllers and the like. Similarly, although the storage device 20 has been described as being a memory device, the present invention is as readily adaptable to any of the other well known forms of bus slave such as peripheral controllers and the like. In addition, more than one different kind of bus slave may be used together to form a composite storage device 20. In such a system, it is quite possible that a particular operand transfer would span an address transition between two such different bus slaves. Depending upon the system configuration, the data port sizes of these bus slaves may be different. However, since the bus controller 14 recomputes the operand alignment, address and residue size on a bus cycle by bus cycle basis, the operand transfer will still be performed correctly even if the reported port size is different for each bus cycle. Thus, the bus controller 14 is fully capable of dynamically sizing the communication bus on a cycle by cycle basis.

We claim:

1. A data processor adapted to communicate with a storage device having any of a plurality of different port sizes using a communication bus which is sized to accomodate each of the different port sizes, the data processor comprising:

first means for providing to the storage device a strobe signal indicating that an operand is to be communicated using the communication bus;

second means for receiving an acknowledge signal, provided by the storage device in response to the strobe signal, indicating that the storage device is prepared to communicate the operand with the data processor using a portion of the communication bus corresponding to a selected one of the different port sizes; and third means for communicating the operand between the data processor and the storage device in as many units of the selected port size as are required to completely communicate the operand, using the portion of the communication bus which corresponds to the selected port size.

2. The data processor of claim 1 wherein the third means communicates each of the units of the operand using the portion of the communication bus during a respective bus cycle.

3. The data processor of claim 2 wherein the first means provides the strobe signal at the start of each of said bus cycles.

4. The data processor of claim 3 wherein the acknowledge signal, provided by the storage device in response to each of the strobe signals, indicates which of the different port sizes the storage device has selected to use in communicating with the data processor during the respective bus cycle; and wherein the third means communicates, during that bus cycle, as much of the operand between the data processor and the storage device as may be accomodated on the portion of the communication bus corresponding to the port size selected by the storage device for that bus cycle.

5. The data processor of claim 2 wherein the first means also provides to the storage device a size signal indicating the size of the operand remaining to be communicated.

6. The data processor of claim 1 wherein the first means also provides to the data processor a size signal indicating the size of the operand to be communicated.

7. A bus master adapted to communicate with a bus slave having any of a plurality of different port sizes using a communication bus which is sized to accomodate each of the different port sizes, the bus master comprising:
- first means for providing to the bus slave a strobe signal indicating that an operand is to be communicated using the communication bus;
- second means for receiving an acknowledge signal, provided by the bus slave in response to the strobe signal, indicating that the bus slave is prepared to communicate the operand with the bus master using a portion of the communication bus corresponding to a selected one of the different port sizes; and
- third means for communicating the operand between the bus master and the bus slave, in as many units of the selected port size as are required to completely communicate the operand, using the portion of the communication bus which corresponds to the selected port size.

8. The bus master of claim 7 wherein the third means communicates each of the units of the operand using the portion of the communication bus during a respective bus cycle.

9. The bus master of claim 8 wherein the first means provides the strobe signal at the start of each of said bus cycles.

10. The bus master of claim 9 wherein the acknowledge signal, provided by the bus slave in response to each of the strobe signals, indicates which of the different port sizes the bus slave has selected to use in communicating with the bus master during the respective bus cycle; and wherein the third means communicates, during that bus cycle, as much of the operand between the bus master and the bus slave as may be accomodated on the portion of the communication bus corresponding to the port size selected by the bus slave for that bus cycle.

11. The bus master of claim 8 wherein the first means also provides to the bus slave a size signal indicating the size of the operand remaining to be communicated.

12. The bus master of claim 7 wherein the first means also provides to the bus slave a size signal indicating the size of the operand to be communicated.

13. In a bus master, a method to communicate with a bus slave having any of a plurality of different port sizes using a communication bus which is sized to accomodate each of the different port sizes, the method comprising the steps of:
- providing to the bus slave a strobe signal indicating that an operand is to be communicated using the communication bus;
- receiving an acknowledge signal, provided by the bus slave in response to the strobe signal, indicating that the bus slave is prepared to communicate the operand with the bus master using a portion of the communication bus corresponding to a selected one of the different port sizes; and
- communicating the operand between the bus master and the bus slave, in as many units of the selected port size as are required to completely communicate the operand, using the portion of the communication bus which corresponds to the selected port size.

14. The method of claim 13 wherein each of the units of the operand is communicated using the portion of the communication bus during a respective bus cycle.

15. The method of claim 14 wherein the strobe signal is provided at the start of each of said bus cycles.

16. The method of claim 15 wherein the acknowledge signal, provided by the bus slave in response to each of the strobe signals, indicates which of the different port sizes the bus slave has selected to use in communicating with the bus master during the respective bus cycle; and wherein, during that bus cycle, as much of the operand is communicated between the bus master and the bus slave as may be accomodated on the portion of the communication bus corresponding to the port size selected by the bus slave for that bus cycle.

17. The method of claim 14 including the step of providing to the bus slave a size signal indicating the size of the operand remaining to be communicated.

18. The method of claim 13 including the step of providing to the bus slave a size signal indicating the size of the operand to be communicated.

* * * * *